US006458962B1

(12) United States Patent
Mao et al.

(10) Patent No.: US 6,458,962 B1
(45) Date of Patent: Oct. 1, 2002

(54) SULTAMS: CATALYST SYSTEMS FOR ASYMMETRIC REDUCTION OF A C=N INTERMEDIATE BIOLOGICAL COMPOSITIONS AND METHODS FOR MAKING THE SULTAMS

(75) Inventors: Jiammin Mao; David C. Baker, both of Knoxville, TN (US)

(73) Assignee: The University of Tennesseee Research Corporation, TN (US)

( * ) Notice: Subject to any disclaimer, the term of this patent is extended or adjusted under 35 U.S.C. 154(b) by 0 days.

(21) Appl. No.: 09/413,054

(22) Filed: Oct. 1, 1999

Related U.S. Application Data

(60) Provisional application No. 60/126,252, filed on Mar. 25, 1999, and provisional application No. 60/150,132, filed on Aug. 20, 1999.

(51) Int. Cl.$^7$ .............................................. C07D 275/06
(52) U.S. Cl. ...................... 548/209; 514/373; 556/137
(58) Field of Search ......................................... 548/209

(56) References Cited

FOREIGN PATENT DOCUMENTS

| DE | 2105580 A | 9/1972 |
|---|---|---|
| WO | WO 98/42643 | 10/1998 |
| WO | WO 00/18708 | 4/2000 |

OTHER PUBLICATIONS

Mashima et al., "Asymmetric Transfer Hydrogenation of Ketonic Substrates Catalyzed by ($\eta^5$–$C_5Me_5$) MC1 Complexes {M=Rh and Ir} of (1S, 2S)–N–(p–Toluenesulfonyl)–1, 2–diphenylethylenediamine", Chemistry Letters, Dec. 1998, No. 12, pp. 1199–1200, especially p. 1199, col. 1, compound 3a.

Mashima et al., "The Half–sandwich Hydride and 16–Electron Complexes of Rhodium and Iridium Containing (1S, 2S)–N–(p–Toluenesulfonyl)–1, 2–diphenylethylenediamine: Relevant to the Asymmetric Transfer Hydrogenation", Chemistry Letters, Dec. 1998, No. 12, pp. 1201–1202, especially p. 1201, the compounds of 1a and 3a.

Baker et al, "A Chiral Rhodium Complex for Rapid Asymmetric Transfer Hydrogenation of Imines with High Enantioselectivity", Organic Letters, vol. 1, No. 6, pp. 841–843, Sep. 23, 1999.

*Primary Examiner*—Laura L. Stockton
(74) *Attorney, Agent, or Firm*—Schnader Harrison Segal & Lewis LLP

(57) ABSTRACT

Biologically active sultams are disclosed which have potent anti-HIV activity. Solution methods of syntheses, which use a new catalyst for the asymmetric reduction of a C=N intermediate, are described. Biological compositions and method of treating mammals for viral infections with compositions comprising the sultams of the invention, especially HIV are described.

47 Claims, 6 Drawing Sheets

VI   VIIa   VIIIa

VI   VIIb   VIIIb

VIIIa'

VIIIb'

SULTAMS: CATALYST SYSTEMS FOR ASYMMETRIC REDUCTION OF A C=N INTERMEDIATE BIOLOGICAL COMPOSITIONS AND METHODS FOR MAKING THE SULTAMS

CROSS-REFERENCE TO RELATED PATENT APPLICATIONS

This application is based on provisional application serial no. 60/126,252, filed under 37 C.F.R. 1.53(b)(2), entitled ASYMMETRIC SYNTHESIS OF SULTAMS AND NOVEL RHODIUM CATALYST, filed on Mar. 25, 1999, and provisional application serial no. 60/150,132, entitled SULTAMS: CATALYST SYSTEMS FOR ASYMMETRIC REDUCTION OF THE C=N INTERMEDIATE BIOLOGICAL COMPOSITIONS METHODS FOR MAKING THE SULTAMS, filed Aug. 20, 1999. This application claims the benefit of the filing dates of these applications. These applications are incorporated herein by reference in their entirety.

STATEMENT REGARDING FEDERALLY SUPPORTED RESEARCH

This invention was made with government support under Contract/Grant N01-CM-67261 awarded by the National Cancer Institute. The government has certain rights in this invention.

BACKGROUND OF THE INVENTION

Acquired immune deficiency syndrome (AIDS) is characterized by a severe deficiency in the helper T cells of the immune system. Human immunodeficiency virus (HIV), which causes AIDS, is a member the lentiviruses that are part of a large group of viruses known as the Retroviridae. Retroviridae also include closely related simian, feline, and bovine immunodeficiency viruses that share a variety of common features.

The fact that HIV has a tendency to mutate to forms that are resistant to existing antiviral therapies greatly complicates attempts to treat the infection with antiviral drugs. Most of the current research in AIDS is aimed at understanding the life cycle of HIV to develop treatments targeted to inhibit the virus at different stages of its life cycle.

The normal flow of genetic information is from DNA to RNA to protein. However, HIV virions carry RNA into their host cell and must first convert their viral genomic RNA into a double-stranded DNA in order to start their replication cycle in the host cell. This conversion is directed in the host cell cytoplasm by a viral enzyme called reverse transcriptase (RT). Thus, RT is an attractive target for HIV inhibitors.

HIV RT inhibitors can be broadly classified into nucleoside and non-nucleoside RT inhibitors. The modes of action of these two classes of compounds are different in nature. The nucleoside HIV RT inhibitors are competitive inhibitors that bind to the catalytic site of the enzyme, and their mode of action appears to be through their triphosphates (produced in the cytoplasm of the host cell) that act as RT enzyme inhibitors through incorporation and termination of the growing viral DNA chain. Common nucleoside RT inhibitors (NRTIs) include AZT, ddC, ddI, d4T, 3TC, and Abacavir. Non-nucleoside reverse transcriptase inhibitors (NNRTIs) are non-competitive inhibitors of the RT enzyme; they bind to an allosteric (regulatory) site and influence the RT catalytic site. Hence, they are also referred to as second-site RT inhibitors. In general, at micromolar concentrations NNRTIs inhibit HIV-1 in vitro with minimum or no cytotoxicity but do not inhibit HIV-2 or other retroviruses. NNRTIs include chloro-TIBO, nevirapine, L-697,661, and delavirdine.

Sultams (2,3-dihydrobenzo[d]isothiazole 1,1-dioxides) are potent NNRTIs. The enantiomeric form of sultams is important to the potency of HIV-1 RT inhibition. Therefore, efficient synthesis of pure enantiomers of the racemates of active sultam compounds is desirable.

The need and research for active inhibitors of human immunodeficiency virus-1 RT is urgent and ongoing.

FIELD OF THE INVENTION

The invention relates to the catalytic synthesis of sultams, which are useful as non-nucleoside inhibitors of reverse transcriptase. In sultam synthesis from saccharin, the most crucial step is the asymmetric reduction of the C=N intermediate, which defines the stereochemistry of the sultam. In accordance with the invention, it is of vital importance to develop a catalyst which would carry out reductions of these imines stereoselectively. Other catalysts of the type have proven to be inefficient for the asymmetric reduction of imines to form sultams, resulting in a low enantiomeric excess (ee). By defination, ee is (excess of one enantiomer over the other enantiomer)/(entire mixture)×100% and is used to express relative amounts of enantiomers in a mixture.

DESCRIPTION OF PUBLICATIONS OF INTEREST

Publications of interest relating to the subject matter of this invention include:
1. Oppolzer, *Tetrahedron Lett.*, 1990, 31, 4117–4120.
2. Uematsu, N.; Fujii, A.; Hashiguchi, S.; Ikariya, T.; Noyori, R. *J. Am. Chem. Soc.*, 1996, 118, 4916–4917.
3. Ahn, K. H.; Ham, C.; Kim, S. -K.; Cho, C. -W. *J. Org. Chem,.* 1997, 62, 7047–7048.
4. Stinson, S. C. C&EN News, page 20, Jun. 1, 1999.
5. Mashima, *Chem. Lett,.* 1998, 1199–1202.
6. Henry et al. *Tetrahedron Lett,.* 1989, 30, 5709–5712.
7. Abramovich et al. *J. Chem. Soc., Perkin Trans.* 1, 1974, 2589.
8. Staehle, H.; Koeppe, H.; Kummer, W.; Zelle, K. German Pat. DE 71-4 2105580, 1971; (1972) *Chem. Abstr.* 77: 164669.
9. Oda, T.; Irie, R.; Katsuki, T.; Okawa, H. *Synlett*, 1992, 641.
10. Wagner, K. *Angew. Chem., Int. Ed. Engl.* 1970, 9, 50.
11. Narita, K.; Sekiya, M. *Chem. Pharm. Bull.* 1977, 25, 135.
12. Doepp, D.; Lauterfeld, P.; Schneider, M.; Schneider, D.; Seidel, U. *Phosphorus, Sulfur, Silicon Relat. Elem.* 1994, 96, 481–482.
13. Guermy, C.; Malleron, J. L.; Mignani, S. Eur. Pat. Appl. EP 429341 A2 910529, 1991.
14. Watanabe, H.; Gay, R. L.; Hauser, C. R *J. Org. Chem.* 1968, 33, 900–903.
15. Meltzer, P. C.; Liang, A. Y.; Brownell, A. -L.; Elmaleh, D. R.; Madras, B. K. *J. Med. Chem.* 1993, 36, 855.
16. Smart, N. G.; Carleson, T.; Kast, T.; Clifford, A. A.; Burford, M. D.; Wai, C. M. *Talanta* 1997, 44, 137–150.
17. Kainz, S.; Brinkmann, A.; Leitner, W.; Pfaltz, A. *J. Am. Chem. Soc.* 1999, 121, 6421–6429.

Of particular interest are publications on other catalytic systems explored in the field of interest.

Oppolzer, et al., discloses preparation of enantiomerically pure sultams (R)-2 and (S)-2 from non-chiral saccharin.

Methyllithium in diethyl ether was added to saccharin to form a prochiral imine which was converted to pure (R)-2 sultam by hydrogenation with the catalyst Ru$_2$Cl$_4$[(R)-(+)-BINAP]$_2$(NEt$_3$) in 72% yield, and was converted to enantiomerically pure (S)-2 sultam using analogous catalyst, (S)-(−)-BINAP in 71% yield.

Noyori and colleagues reported a catalyst system based on ruthenium which was used for a series of carbonyl and imine hydrogen-transfer reductions on some heterocyclic compounds. In these systems, the outcome of the reduction could be predicted. (R)-isomers were generated using an (S,S)-catalyst, and (S)-isomers were generated using an (R,R)-catalyst. Both the preformed catalyst precursor and the true catalyst were reported.

Ahn et al. (1997) *J. Org. Chem.* 62: 7047–7048 obtained results for some sultams that were directly opposite to those predicted by Noyori's rule when the Noyori catalysts were used. In Ahn's system, when the the 3-substituents were alkyl (e.g., Me- or t-Bu) or aryl (e.g., benzyl), the (S,S)-catalyst gave (S)-isomers. Therefore, the approach of the catalyst to the C=N center comes from opposite directions in the Noyori system from that of the Ahn system.

Stinson (1998) *Chem. & Eng. News* 76 (22):15–24, reported a rhodium-based catalyst for highly enantioselective reductions of carbonyls and imines.

Mashima et al. (1998) *Chem. Letters* 1199–1202, reported rhodium and iridium complexes of(1S,2S)-N-(p-toluenesulfonyl)-1,2-diphenylethylenediamine which functioned as catalyst precursors for asymmetric transfer hydrogenation. The catalyst had an (S,S) structure, and the reductions carried out were limited to carbonyl group reductions such as the conversion of C=O to CH—OH.

Most recently, Pfaltz and coworkers report high enantioselectivity when iridium-catalyzed hydrogenation of prochiral imines were performed in supercritical carbon dioxide. The phase behavior of the reaction mixture and the increased solubility of the catalyst in solution were key to the improved selectivity. This new solvent system has the added advantage of being environmentally friendly.

All references referred to in this text are incorporated herein by reference in their entirety.

SUMMARY OF INVENTION

Catalytic asymmetric reduction of multiple bonds has received much attention in recent years- in particular, asymmetric hydrogenation due, in part, to the importance of optically active amines as pharmaceuticals and agrochemicals. Among the methods available for reductions, asymmetric transfer hydrogenation has advantages over other processes in operational simplicity that avoids the use of gaseous hydrogen. In recent years C$_2$-symmetric diamine-ruthenium(II) complexes have been advanced for overcoming the relatively low reactivities observed for the transfer hydrogenation of imines. Of particular importance is the ability to effect catalytic transfer hydrogenation of the imines stereoselectively since the chirality of the resulting sultam is pivitol to the biological activity of the compound.

The invention provides pre-catalysts and catalysts which are suitable for the efficient synthesis of enantiomerically pure forms of sultams which may be used as HIV RT inhibitors.

The invention also provides a method for preparing enantiomerically pure sultams suitable for use as HIV RT inhibitors.

An objective of the synthesis was to obtain biologically active compounds, especially anti-HIV-1 compounds. The sultam compounds of the invention offer a variety of structural modifications and various possibilities of positioning different substituents in different positions on any one of the rings. It was not known prior to this invention what effect these various substituents and their different positions on the nitrogen, on the stereogenic carbon, and on the ring(s) would have on their biological and, more particularly, their anti-HIV-1 activity.

The invention also provides a new class of such compounds in enantiomerically enriched form which can be purified into their respective enantiomers. A group of these compounds has an anti-HIV potency heretofore unachieved for this class of compounds. In accordance with the invention, an area of the molecule has been identified on which appropriate substituents appear to make a major contribution to a high degree of anti-HIV potency.

The invention also provides a method for treating or preventing viral infections, especially strains of the HIV virus, with the sultams of the invention.

The invention also provides biologically active compositions, which comprise one or more compounds of the invention, in an effective, non-toxic amount in combination with a biologically or pharmaceutically acceptable carrier.

The invention also provides drug combinations of compounds of the invention with HIV protease inhibitors, like ritonavir, saquinavir mesylate, and others.

In still another aspect, the invention provides a method for treating a mammal, particularly a human, infected with a retrovirus, which comprises administering to said mammal an effective nontoxic amount of the composition(s) of the invention.

In summary, the invention contributes to the solution for a serious and urgent world-wide health need which has adverse social and economic consequences.

DETAILED DESCRIPTION OF THE INVENTION

The Catalyst Of The Invention

Figure 1:
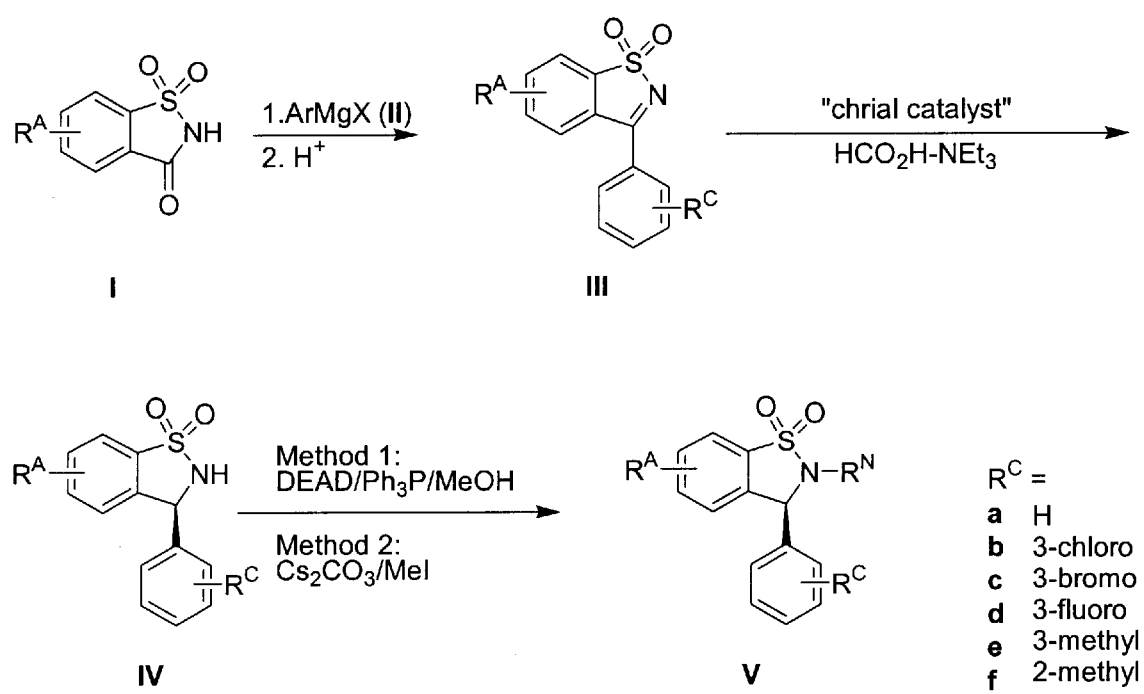
FIG. 1 shows the synthesis of chiral sultams from saccharin.
Figure 2A:
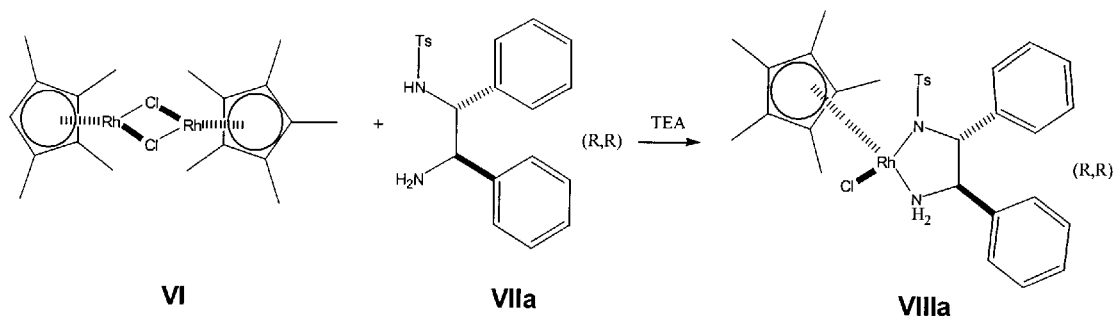
FIG. 2a shows the synthesis of catalyst precursor (S)-RhClCp*[(1R,2R)-p-TsNCH(C$_6$H$_5$)CH(C$_6$H$_5$)NH$_2$] from [RhClCp*]$_2$ and (R,R)-N-p-toluenesulfonyl-1,2-diphenylethylenediamine.
Figure 2B:
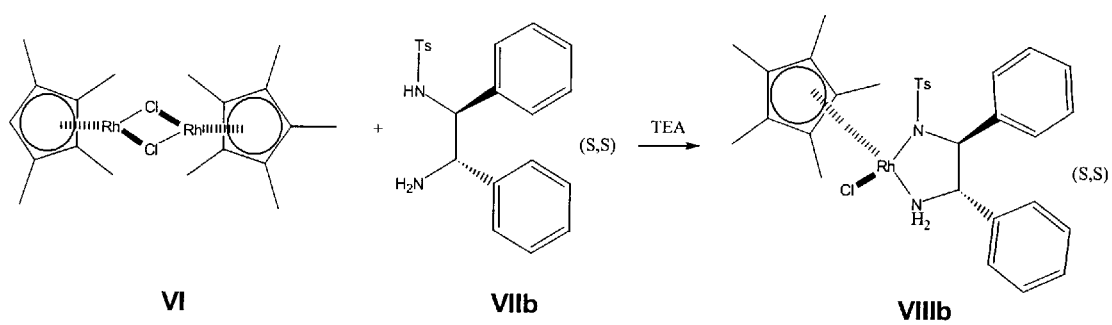
FIG. 2b shows the synthesis of catalyst precursor (R)-RhClCp*[(1S,2S)-p-TsNCH(C$_6$H$_5$)CH(C$_6$H$_5$)NH$_2$] from [RhClCp*]$_2$ and (S,S)-N-p-toluenesulfonyl-1,2-diphenylethylenediamine.
Figure 2C:
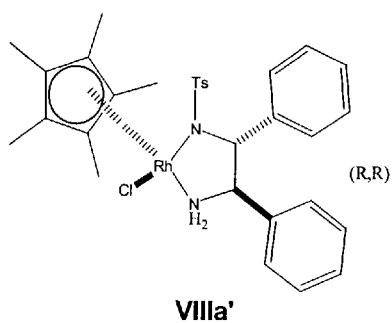
FIG. 2c shows the (R,R) catalyst.
Figure 2D:
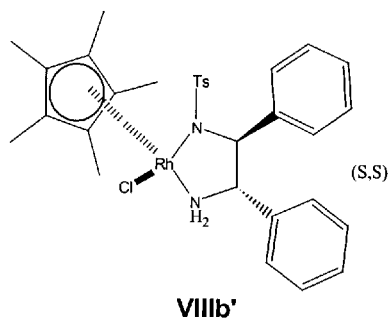
FIG. 2d shows the (S,S) catalyst.

The catalyst of the invention is a 16-electron Ru(II) diamide complex comprising a N-tosylated 1,2-diamine ligand. However, whereas other catalysts use $\eta^6$-arenes such as benzene, cymenes or substituted benzene rings, the catalyst of the invention utilizes pentamethylcyclopentadienyl ($\eta^5$-$C_5R_5$) in place of the $\eta^6$-arene ligand.

There are three chiral centers on the catalyst: one on the metal center and two which comprise the TsDPEN ligand. The interaction of the ligand with the metal determines chirality on the metal. Thus, (S,S) in the TsDPEN forms R on the metal as the exclusive product, which although technically is a diastereomer, cannot be reversed by a known method. As a result, the stereochemistry of the final catalyst is determined by the stereochemistry of the N-p-toluenesulfonyl-1,2-diphenylethylenediamine (TsDPEN) ligand used in its formation. Therefore, reaction of rhodium complex [RhClCp*]$_2$ with (R,R)-TsDPEN gives the (R,R) catalyst, while reaction with (S,S)-TsDPEN gives the (S,S) catalyst.

The catalyst precursor (S)-RhClCp*[(1R,2R)-p-TsNCH($C_6H_5$)CH($C_6H_5$)NH$_2$] having the structure (VIIIa)

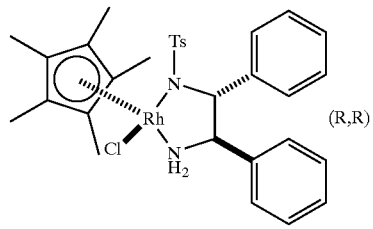

VIIIa may be formed in situ or used preformed in accordance with the invention.

The catalyst of invention is generated during the reaction from the catalyst precursor. Thus the active form of the (R,R) catalyst has structure (VIIIa').

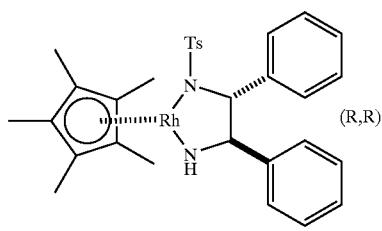

VIIIa'

The catalyst precursor (R)-RhClCp*[(1S,2S)-p-TsNCH($C_6H_5$)CH($C_6H_5$)NH$_2$] having the structure (VIIIb)

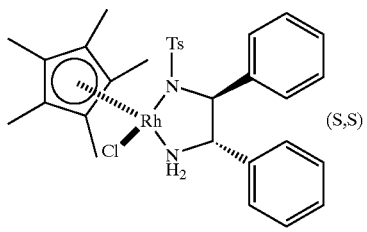

VIIIb may be formed in situ or used preformed in accordance with the invention.

Thus the active form of the (S,S) catalyst has structure (VIIIb').

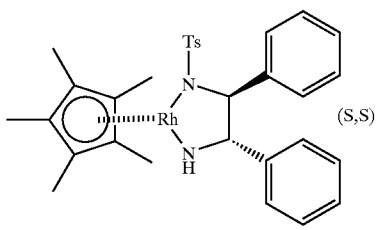

VIIIb'

In contrast to Noyori's catalyst, the (R,R) form of the catalyst in accordance with the invention gives (S) product while the (S,S) form of the catalyst gives (R) product. It should be noted that a substituent like Cl at position-2 reverses the Cahn-Ingold-Prelog priorities, giving R for the center that is stereochemically equivalent to the S center for the other compounds. The ee's for these reactions were modest, ranging from 68–75%; however, by simple crystallization of the enriched mixtures, pure (+)-(S)-compounds can be obtained.

Table I gives a comparison of Noyori's catalyst as compared to the catalyst of invention as applied to certain substrates.

TABLE I

Reaction conditions and results

| imine | ligand (N[a]) | S/C[b] (N) | T ° C. (N) | time (N) | % ee (N) | config. |
|---|---|---|---|---|---|---|
| IIIa | R,R (S,S) | 200 (100) | 20 (28) | 40 min (3 h) | 86 (68) | S |
| IIIb | R,R (S,S) | 200 (100) | 20 (28) | 30 min (3 h) | 81 (69) | S |
| IIId | R,R (S,S) | 200 (100) | 20 (28) | 25 min (3 h) | 85 (75) | (+) |
| IIIe | R,R (S,S) | 200 (100) | 20 (28) | 10 min (3 h) | 95 (74) | (+) |

[a]N = Noyori method.
[b]S = substrate, C = catalyst

As shown in Table I, column 3, the rhodium catalyst can be used in a substrate to catalyst ratio of 200 whereas Noyori's catalyst is typically used with a substrate to catalyst ratio of 100. Column 4 typifies reaction temperature of the catalyst of the invention which works well at about 20° C., whereas Noyori's catalyst requires a temperature of 28° C. Importantly, the rhodium catalyst can withstand reaction temperature ranging from about −20 to 40° C. and shows no decrease in enantioselectivity over this range. Required reaction times of the catalyst of the invention are significantly shorter (column 5), and the enantiomeric excess of the catalyst is superior to that of Noyori's ruthenium catalyst (column 6).

In summary, a higher substrate-to-catalyst ratio (S/C) and the ability to use the catalyst of the invention at lower temperatures produces the desired reaction in less time and giving superior enantiomeric excess compared to Noyori's catalyst. As an added advantage, the catalyst precursor of the invention has been stored in a bottle in a desiccator at room temperature for over three months, whereas, in general, such noble metal catalysts are considered air-sensitive. The catalyst is efficient not only for the reduction of imines but for carbonyl compounds as well and has been proven to be highly efficient in the preparation of optically pure sultams with important biological activity.

Method of Invention

Preparation of Rhodium Catalyst Precursors

Preferably, preformed (R,R) catalyst maybe prepared as follows. Triethylamine is added to a solution of rhodium complex [RhClCp*]$_2$ (VI) and (1R,2R)-N-p-toluenesulfonyl-1,2-diphenylethylenediamine[(R,R)-TsDPEN] (VII) in a suitable solvent under inert atmosphere and allowed to stir for about 20 minutes at about 20° C. Generally, the [RhClCp*]$_2$ and (1R,2R)-N-toluenesulfonyl-1,2-diphenylethyenediamine are provided in a halogenated hydrocarbon, such as dichloromethane. Other suitable solvents include toluene, benzene, chloroform, ether, hexane and lower alkanes and halogenated lower alkanes with acetonitrile being the solvent of choice. The molar ratio of [RhClCp*]$_2$ to (R,R)-TsDPEN is generally about 1:2. Although the reaction time and temperature is not particularly limited, the reaction is generally allowed to occur for about 5 minutes to 1 hour, or preferably for about 10–30 minutes, or most preferably for about 20 minutes. Generally, the temperature of the reaction is about 10–30° C., or preferably about 15–25° C., and most preferably about 20° C.

Supercritical carbon dioxide (sCO$_2$) may also be used as a solvent. This avoids the use of toxic solvents like acetonitrile and dichloromethane and therefore makes the process more environmentally friendly.

A base is added in an inert atmosphere, such as under nitrogen, to deprotonate (R,R)-TsDPEN, thereby allowing the amine of the ligand to react with the rhodium complex extruding chloride. Suitable bases include alkali hydroxides, such as potassium hydroxide, sodium hydroxide, and the like, sodium methoxide, sodium bicarbonate, trialkyl amines, heterocyclic amines, such as pyridine, and the like. Triethylamine is the preferred base owing to its volatility and ease of purification.

The reaction solution is washed with water to remove excess starting material followed by evaporation of solvent yielding the catalyst in crude form. Recrystallization from chloroform-hexanes results in the isolation of the pure catalyst precursor in high yields. The (S,S) form of the new catalyst is similarly prepared. This procedure is in contrast to the procedure disclosed in Mashima et al. (ref. 5). In that procedure, [RhClCp*]$_2$ (VI) and two equivalents of (S,S)-TsDPEN were reacted in dichloromethane with an excess of aqueous potassium hydroxide solution.

Preferably, preformed (S,S) catalyst maybe prepared as follows. Triethylamine is added to a solution of rhodium complex [RhClCp*]$_2$ (VI) and (1S,2S)-N-p-toluenesulfonyl-1,2-diphenylethylenediamine[(S,S)-TsDPEN] (VIIb) in a suitable solvent under inert atmosphere and allowed to stir for about 20 minutes at about 20° C. The reaction conditions and suitable bases and solvents are the same as those set forth above for the (S)-RhClCp*[(1R,2R)-p-TsNCH(C$_6$H$_5$)CH(C$_6$H$_5$)NH$_2$] catalyst precursor.

Preparation of Imine Intermediates of Sultams

The catalysts of the invention may be used to produce various sultams. Referring to FIG. 1, the preparation of the sultam represented by compound (V) comprises the following reaction steps. Saccharin (I) is reacted with aryl Grignard reagent (II) and imine (III) is allowed to form in an aprotic solvent as described in the prior art. The Grignard reagent (II) is added slowly, preferably over about a 20 minute period and preferably with agitation of the reaction mixture. The duration and temperature of the reaction can be varied, with about 12 hours duration and a temperature range of about 17–26° C. being the preferred conditions. Other organometallic reagents such as organolithium reagents may also be used instead of Grignard compounds.

Since Grignard compounds react with protic solvents, water, such as atmospheric moisture, should be excluded. Therefore, the reaction with the Grignard reagent should be conducted in an inert gas atmosphere, such as dry nitrogen or argon. The Grignard reagent (II) is an aryl halide where $R^C$ can be any halogen or a lower alkyl, preferrably of 1 to 4 carbon atoms, linear or branched or cycloalkyl. Suitable Grignard reagents include phenylmagnesium bromide, 3-chlorophenylmagnesium bromide, 3-bromophenylmagnesium bromide, 3-fluorophenylmagnesium bromide, 3-methylphenylmagnesium chloride, 2-methylphenylmagnesium bromide, and the like. Upon completion, ice is added to the reaction mixture and the pH is adjusted to pH 1 with 1 M hydrochloric acid. The ice is necessary since heat is generated upon addition of acid. Work-up may be by any standard means known in the art. For example, the resulting solution is washed repeatedly with ether. Subsequently, the ether solution containing the desired product is washed with sodium bicarbonate, and the solution dried with sodium sulfate. The target imine (III) can then be treated to remove the solvent under reduced pressure. Recrystallization gives the pure compound.

The above procedure may also be performed using an appropriately substituted phenyllithium reagent rather than the Grignard reagent.

Asymmetric Transfer Hydrogenation

Asymmetric transfer hydrogenation may be performed by two methods: using Noyori's catalyst, RuCl(TsDPEN)(cymene), or using the catalysts of the invention. Use of Noyori's catalyst results in enantiomerically pure compound (IV) after purification. Thus, the catalyst is formed in situ by heating the precatalyst [RuCl$_2$($\eta^6$-p-cymene)]$_2$ and triethylamine at 80° C. preferably with agitation. After about 1 hour, the reaction is allowed to cool to room temperature and sulfonylimine (III), in solvent, is added to the solution of catalyst. Addition of an azeotropic mixture of 5:2 formic acid-triethylamine at about 25° C. results in the formation of the desired sultam.

The duration of the reaction can be varied from 1 hour to 12 hours, with 1 hour being the preferred duration.

Suitable solvents for use in the invention include dichloromethane, toluene, benzene, chloroform, ether, hexane and lower alkanes, halogenated lower alkanes, and the like. Among the suitable solvents, acetonitrile is preferred. Supercritical CO$_2$ may also be used.

Upon completion of the reaction, sodium bicarbonate is added to the solution to render the solution basic, and the resulting solution is extracted with ethyl acetate. The ethyl acetate solution containing the desired sultam may be treated to remove solvent under reduced pressure. Purification by column chromatography followed by recrystallization in ethyl acetate-hexanes gives the pure product. The formation of the sultam can be monitored by thin-layer chromatography.

Alternatively, asymmetric transfer hydrogenation can be effected using a catalyst of the invention. Asymmetric reduction can be performed using a preformed catalyst or by forming the catalyst in situ. Referring to FIG. 1, sulfonylimine (III) is reacted with preformed catalyst precursor (S)-RhClCp*[(1R,2R)-p-TsNCH($C_6H_5$)CH($C_6H_5$)$NH_2$] (VIIIa) in solvent upon addition of an azeotropic mixture of 5:2 formic acid-triethylamine at about 25° C. The duration of the reaction can be varied from 1 hour to 5 hours. Suitable solvents include dichloromethane, toluene, benzene, chloroform, ether, hexane and lower alkanes and halogenated lower alkanes, with acetonitrile being the preferred solvent. Upon completion of the reaction, sodium bicarbonate is added to the solution to render the solution basic, and the resulting solution is extracted with dichloromethane. Subsequently, the dichloromethane solution is washed with a saturated sodium chloride solution and then dried with magnesium sulfate. The target compound (IV) can then be treated to remove the solvent under reduced pressure. Purification by column chromatography gives the pure product. The formation of the sultam can be monitored by thin-layer chromatography.

The precatalyst can also be generated in situ by allowing the rhodium dimer (VI) and chiral ligand (VII) to react with triethylamine under inert atmosphere (FIG. 2), preferably with agitation. A reaction duration of 20 minutes and a temperature range of about 17–26° C. are preferred. The desired compound (IV) is obtained upon addition of the appropriate sulfonylimine (III) and an azeotropic mixture of 5:2 formic acid-triethylamine at about 25° C. The remainder of the procedure is identical to that described for using the preformed catalyst. (R,R) catalyst gives S sultam and (S,S) catalyst gives R sultam.

Methylation of the Sultam Nitrogen Atom

Finally, N-methylation may be effected by one of two methods: by the Mitsunobu method disclosed by Henry et al. (ref. 6), or by a method involving treatment with cesium carbonate. In the Mitsunobu method, a reaction is effected by the slow addition of 1.5 equivalents of diethyl azodicarboxylate to a solution of the starting secondary amine (IV), 1.5 equivalents of triphenylphosphine and 1.5 equivalents of methanol in solvent under inert atmosphere preferably with agitation. Reaction duration is preferably about 15 minutes with the preferred temperature range being about 17–26° C. Suitable solvents include tetrahydrofuran and the like. The alkylated sultam can then be treated to remove solvent under reduced vacuum. Purification by column chromatography followed by recrystallization in ethy acetate-hexanes gives the pure product. The formation of the alkylated product can be monitored by thin-layer chromatography. Alternatively, in a cesium carbonate method, compound (IV) can be treated with 1.3 equivalents of cesium carbonate preferably with agitation. Reaction duration is preferably about 30 minutes with the preferred temperature range being about 17–26° C. Suitable solvents include N,N-dimethylformamide and other aprotic polar solvents. Subsequently, 1.3 equivalents of an alkyl iodide is added and the solution is allowed to react. Reaction duration is preferably about 1 hour with the preferred temperature range being about 17–26° C. Suitable alkyl iodides include methyl iodide, ethyl iodide, butyl iodide, 2-propyl iodide, and the like. Cycloalkyl halides, alkyl chlorides and bromides will function suitably as well. Of the alkyl iodides suitable for use in the invention, methyl iodide is preferred. Upon the completion of the reaction, the solution is poured into cold water. The cold water is necessary to safely destroy any excess reagents. The desired alkylated sultam can be filtered off and dried. Purification by recrystallization from ethyl acetate-hexanes gives the pure compound. For the addition of simple alkyl groups, like methyl, which cannot undergo elimination as a side reaction, the direct alkylation method is preferred. The Mitsunobu procedure is preferred for all other alkylations.

Figure 3:
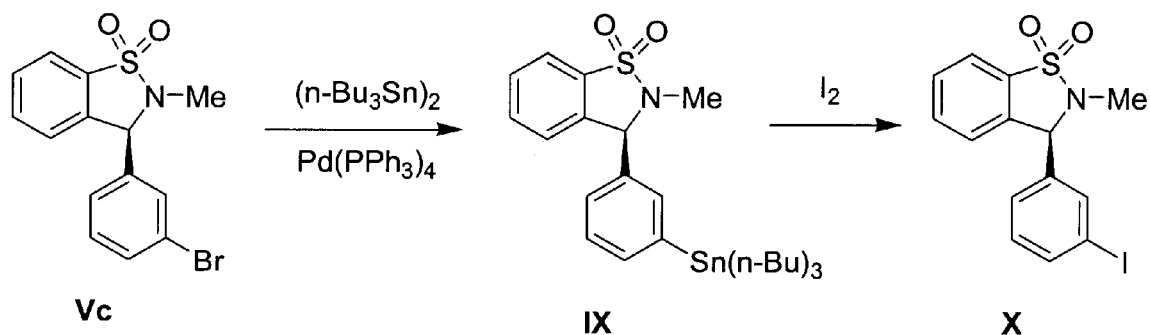
FIG. 3 shows the synthesis of iodinated, methylated sultam from a corresponding brominated, methylated sultam.
Figure 4:
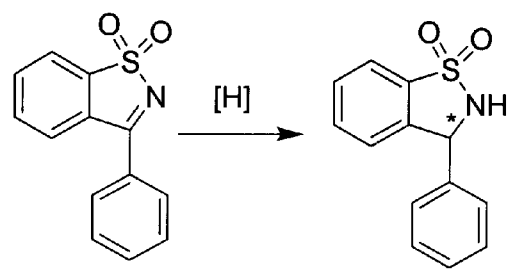
FIG. 4 shows asymmetric transfer hydrogenation of the C=N bond of a sultam intermediate.
Figure 5:
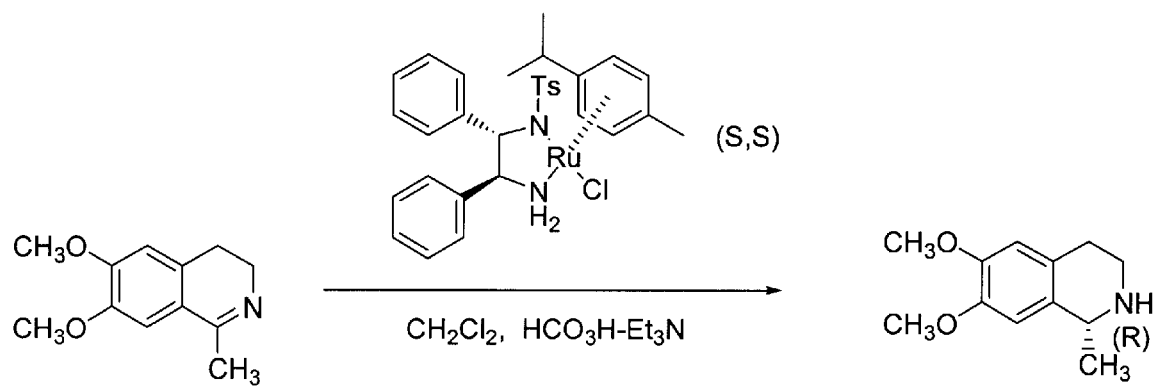
FIG. 5 shows imine reduction of heterocyclic compounds according to the method of Noyori (ref. 2) using ruthenium-containing (S,S) catalysts to make (R)-isomers and (R,R) catalysts to produce (S)-isomers.
Figure 6:
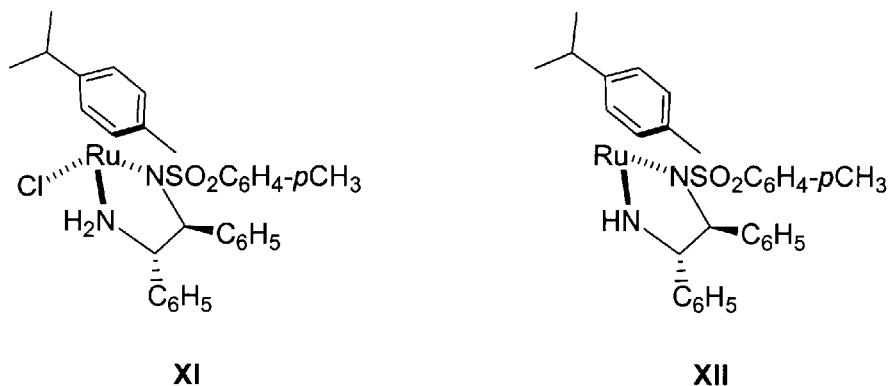
FIG. 6 shows the structure of the Noyori precatalyst and catalyst.
Figure 7:
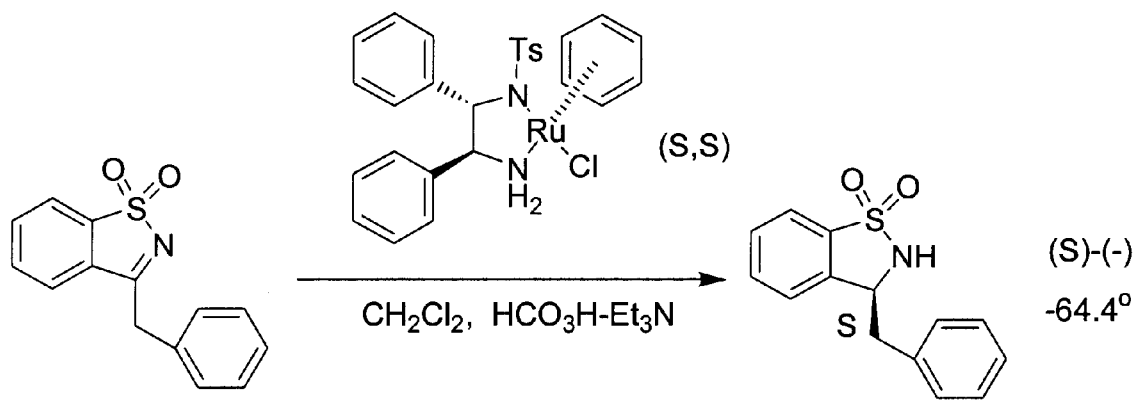
FIG. 7 shows catalytic production of (S)-isomers from a ruthenium-containing (S,S) catalyst on 3-benzyl-substituted sultams according to Ahn (ref. 3).
Figure 8:
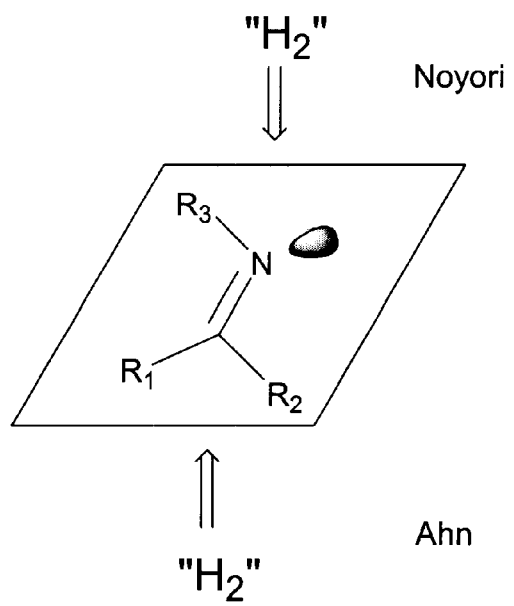
FIG. 8 shows how the approach of the Noyori catalyst and the Ahn catalyst to the imine bond differs during reduction.
Figure 9:
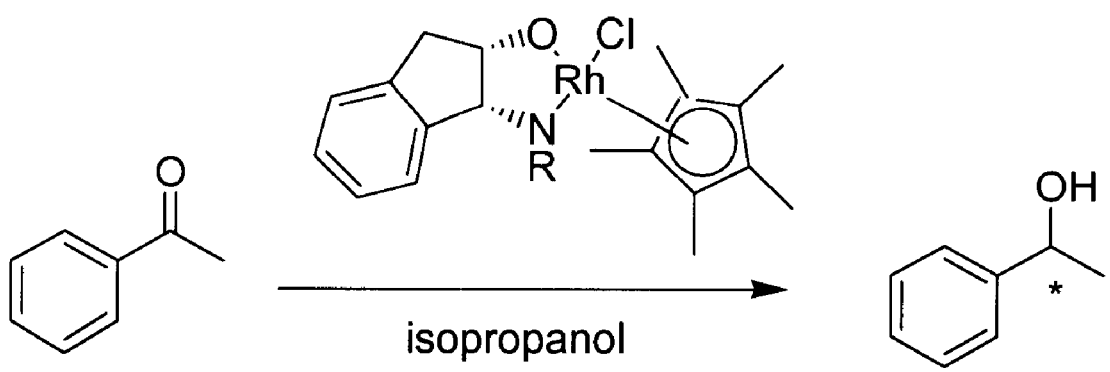
FIG. 9 shows use of a rhodium-containing catalyst for enantioselection for carbonyl and imine reduction according to Stinson et al.

Preparation of 3-(3-Iodophenyl)sultam Unfortunately, the synthesis of the 3-(3-iodophenyl)sultam (X) was not practical via the iodophenyl Grignard (or organolithium). Preparation of iodophenyl Grignard reagents proceed in very low yields. Instead, the 3-(3-iodophenyl)sultam (X) requires the conversion of the 3-(3-bromophenyl)sultam (Vc) to the 3-(3-tributylstannylphenyl) derivative followed by iodination with iodine (FIG. 3). Thus, compound (Vc) and a catalytic amount of tetrakis(triphenylphosphine) palladium were dissolved in degassed toluene. Solvents can be degassed by applying a vacuum from a water aspirator at room temperature. Tributylstannane is then added dropwise to the reaction solution and the resulting solution was degassed for another ten minutes preferably with agitation. Again the about 17–26° C. temperature range is preferred. The mixture is brought to reflux which is maintained for a duration of about four hours.

The resulting stannane (IX) can then be treated to remove the solvent under reduced pressure. Purification by column chromatography gives pure compound. Finally, iodination is effected by treating a degassed solution of stannane (IX) in dichloromethane with iodine under inert atmosphere preferably with agitation. The duration and temperature of the reaction can be varied, with about 12 hours being the preferred duration and the temperature range of about 17–26° C. being preferred. Upon completion, the reaction is treated with 1% aqueous sodium thiosulfate to get rid of excess iodine and the aqueous layer is extracted with dichloromethane. The dichloromethane solution was dried over magnesium sulfate and treated to remove solvent under reduced pressure. Purification by column chromatography gave the pure product (X).

The Compounds of the Invention

Illustrative Sultams of the Invention

The sultams of the invention include the compounds of formula V, as shown in FIG. 1, in which $R^A$ is hydrogen, a linear- or a branched-chain hydrocarbon (saturated or unsaturated) such as alkyl, preferably lower alkyl, cycloalkyl or a halogen such as chlorine, bromine, iodine, or fluorine.

$R^N$ is hydrogen, a linear- or branched-hydrocarbon (saturated or unsaturated) such as alkyl, preferably lower alkyl or cycloalkyl.

$R^C$ is hydrogen, a linear- or branched-hydrocarbon (saturated or unsaturated), such as alkyl, preferably lower alkyl, a halogen such as chlorine, bromine, iodine, or fluorine, hydroxyl, alkoxyl, preferably lower alkoxyl, or an amide such as an acylamide.

Ring C can also be a heterocyclic or polycyclic aromatic ring provided that the corresponding Grignard reagent can by synthesized and is reactive in the reaction. Ring A may contain alkyl, aryl, or related groups as substituents. Ring A may be mono-, di-, or even tri-substituted. Fused systems are also acceptable.

The sultam in which all substituents are hydrogen, but for $R^N$, which is methyl, namely (±)-2-methyl-3-phenyl-2,3-dihydrobenzo[d]isothiazole 1,1-dioxide, is a known compound as disclosed by Watanabe et al. The compound is included among the compounds made by the synthesis of the invention because, as far as is known, it had never been made by this method.

Typical compounds of the invention with their respective substituents are shown in Table II. Other compounds of the invention can be synthesized using other reactants that will yield the corresponding substituents on the target sultams.

TABLE II

| Compound | $R^A$ | $R^N$ | $R^C$ | Config. |
|---|---|---|---|---|
| 1 | H | H | H | (+)-(S) |
| 2 | H | H | H | (−)-(R) |
| 3 | H | H | 3-Cl | (+)-(S) |
| 4 | H | H | 3-Cl | (−)-(R) |
| 5 | H | Me | H | (+)-(S) |
| 6 | H | Me | H | (−)-(R) |
| 7 | H | Me | 3-Me | (+)-(S) |
| 8 | H | Me | 3-Me | (−)-(R) |
| 9 | H | Me | 3-Br | (+)-(S) |
| 10 | H | Me | 3-Br | (−)-(R) |
| 11 | H | Me | 3-Cl | (+)-(S) |
| 12 | H | Me | 3-Cl | (−)-(R) |
| 13 | H | Me | 3-F | (+)-(S) |
| 14 | H | Me | 3-F | (−)-(R) |
| 15 | H | Me | 3-I | (+)-(S) |
| 16 | H | Me | 3-I | (−)-(R) |
| 17 | H | Me | 3-$CF_3$ | (+)-(S) |
| 18 | H | Me | 2-Me | (+)-(S) |
| 19 | H | Me | 2-Me | (−)-(R) |
| 20 | H | Me | 4-Me | (+)-(S) |
| 21 | H | Me | 4-Me | (−)-(R) |
| 22 | H | Me | 4-Br | (+)-(S) |
| 23 | H | Me | 4-Br | (−)-(R) |
| 24 | H | Me | 2-Cl | (+)-(S) |
| 25 | H | Me | 2-Cl | (−)-(R) |
| 26 | H | Me | 4-Cl | (+)-(S) |
| 27 | H | Me | 4-Cl | (−)-(R) |
| 28 | H | Me | 4-F | (+)-(S) |
| 29 | H | Me | 4-F | (−)-(R) |
| 30 | H | Me | 4-OMe | (+)-(S) |
| 31 | H | Me | 4-OMe | (−)-(R) |
| 32 | H | Me | 2-Me, 5-Me | (+)-(S) |
| 33 | H | Me | 2-Cl, 3-Cl | (+)-(S) |
| 34 | H | Me | 2-Cl, 6-Cl | (+)-(S) |
| 35 | H | Me | 4-Ph | (+)-(S) |
| 36 | H | Me | $F_5$ | (+)-(S) |
| 37 | H | Et | 3-Cl | (+)-(S) |
| 38 | H | Bu | 3-Cl | (+)-(S) |
| 39 | H | t-Bu | H | (+)-(S) |
| 40 | H | Ph | H | (+)-(S) |
| 41 | H | 2-Pr | H | (+)-(S) |
| 42 | 5-Me | Me | H | (+)-(S) |
| 43 | 5-Me | Me | 3-Cl | (+)-(S) |
| 44 | 5-Me | Me | 4-F | (+)-(S) |
| 45 | 5-Me | Me | H(a) | (+)-(S) |
| 46 | 5-Me | Me | 4-OMe | (+)-(S) |
| 47 | 5-Cl | Me | H | (+)-(S) |
| 48 | 5-Cl | Et | H | (+)-(S) |
| 49 | 5-Cl | Pr | H | (+)-(S) |
| 50 | H | Me | 3-Et | (+)-(S) |
| 51 | H | Me | 3-vinyl | (+)-(S) |

(a) The ring is furyl.

The following examples are provided to illustrate various aspects of the invention and are not intended to limit the scope of the invention, which is defined in the appended claims.

EXAMPLES

Compounds can be made in accordance with the method of the invention.

Preparation of the Rhodium Catalyst Precursors (S)-RhClCp*[(1R,2R)-p-TsNCH($C_6H_5$)CH($C_6H_5$)$NH_2$] (VIIIa). To a solution of [$RhCl_2$Cp*]$_2$ (309 mg, 0.5 mmol) and (1R,2R)-N-p-toluenesulfonyl-1,2-diphenylethylenediamine [(R,R)-TsDPEN] (366 mg, 1 mmol) in dichloromethane (10 mL), triethylamine (202 mg, 2 mmol) was added under nitrogen. The solution was stirred for 20 min at 20° C., washed with water (5 mL), and dried over $MgSO_4$. Removal of solvents gave the crude product. Recrystallization from chloroform-hexanes afforded red crystals (575 mg, 91%): mp 221–224° C. (dec); $[\alpha]_D^{20}$ −224° (c 0.3, $CHCl_3$); IR (KBr): 3449 (H—N, br), 3281, 3209 (H—N, M) $cm^{-1}$; ESIMS: m/z (%) 639 (1) [$M^+$+1], 603 [$M^+$+1−HCl], 367 (100); $^1$H NMR ($CDCl_3$): δ 1.86 (s, 15H; $CH_3$ in Cp*), 2.22 (s, 3H; $CH_3$ in p-Ts), 3.32 (m, 1H; NHH), 3.71 (m, 1H; HCN$H_2$), 3.97 (d, J=11 Hz, 1H; HCN-p-Ts), 4.03 (m, 1H; NHH), 6.64–7.61 (m, 14H; ArH); $^{13}$C NMR ($CDCl_3$): δ 9.65 ($CH_3$ in Cp*); 21.2 ($CH_3$ in p-Ts), 69.4 (CN$H_2$), 71.8 (CN-p-Ts), 93.9, 94.0, 126.4, 126.7, 127.0, 127.7, 126.2, 128.4, 128.6, 139.2, 139.3, 139.7, 140.6. Anal. Calcd for $C_{31}H_{36}ClN_2O_2RhS$: C, 58.26; H, 5.68; Cl, 5.55; N, 4.38; S, 5.02. Found: C, 58.18; H, 5.67; Cl, 5.69; N, 4.29; S, 4.92.

(R)-RhClCp*[(1S,2S)-p-TsNCH($C_6H_5$)CH($C_6H_5$)$NH_2$] (VIIIb). Prepared similarly to (VIIIa). mp 221–224° C. (dec); $[\alpha]_D^{20}$ +222° (c 0.3, $CHCl_3$). The IR and NMR data were identical with those for the (S)-catalyst in A, above.

Preparation of Imine Intermediates of Sultams

General Method for 3-Aryl-1,2-benzisothiazole 1,1-Dioxides (III). The method is adapted from that of Abramovich et al. (ref. 7). To a solution of saccharin (I, 3.66 g, 20 mmol) in dry THF (250 mL) was added a solution of the Grignard reagent (44 mmol, prepared from the appropriate bromoaryl compound and Mg in $Et_2O$) under nitrogen over a period of 20 min. The solution was stirred at ambient temperature overnight. Ice water (150 g ice) was added to the solution, and the pH was adjusted to pH 1 with 1 M HCl. The organic phase was separated, and the aqueous phase was extracted with ether (4×60 mL). The combined ether extracts were washed with 0.5 M $Na_2CO_3$ (2×50 mL). Evaporation of the dried ($Na_2SO_4$) ether solution gave a solid, which was recrystallized from ethanol or ethyl acetate-hexanes. Compounds IIIa–f were similarly prepared.

Alternatively, for examples IIIa, IIId, IIIe, and IIIf, the corresponding substituted phenyllithium reagent (prepared from the aryl halide and lithium in THF) can be substituted for the Grignard reagent with equivalent results.

3-Phenyl-1,2-benzisothiazole 1,1-Dioxide (IIIa). Yield: 80%; mp 167° C.; $^1$H NMR ($CDCl_3$): δ 7.58–8.04 (9H, m, ArH); $^{13}$C NMR ($CDCl_3$): δ 123.06, 126.55, 129.21, 129.49, 130.43, 130.55, 133.37, 133.60, 141.14 (Ar), 170.99 (C=N).

3-(3-Chlorophenyl)-1,2-benzisothiazole 1,1-Dioxide (IIIb). Yield: 76%; mp 149–150° C. (ethanol). $^1$H NMR ($CDCl_3$): δ 7.57–8.04 (8H, m, ArH); $^{13}$C NMR ($CDCl_3$): δ 123.24, 126.27, 127.52, 129.34, 130.05, 130.55, 132.02, 133.32, 133.65, 133.78, 135.47, 141.03 (Ar), 169.77 (C=N).

3-(3-Bromophenyl)-1,2-benzisothiazole 1,1-Dioxide (IIIc). Yield: 57%; mp 170° C. (ethyl acetate-hexanes). $^1$H NMR ($CDCl_3$): δ 7.47–8.10 (8H, m, ArH); $^{13}$C NMR ($CDCl_3$): δ 123.20, 123.28, 126.28, 127.92, 129.98, 130.71, 132.15, 133.39, 133.65, 133.83, 136.22, 140.93 (Ar), 169.64 (C=N); MS: (m/z) 323,321 ($M^+$, 82%), 257 (M-$SO_2$, 52), 178 (100). Anal. Calcd for $C_{13}H_8BrNO_2S$: C, 48.47; H, 2.50; N, 4.35. Found: C, 49.21; H, 2.46; N, 4.25.

3-(3-Fluorophenyl)-1,2-benzisothiazole 1,1-Dioxide (IIId). Yield: 74%; mp 137° C. (ethyl acetate-hexanes). $^1$H NMR ($CDCl_3$): δ 7.40–8.04 (8H, m, ArH); $^{13}$C NMR ($CDCl_3$): δ 116.27, 116.65, 120.27, 120.61, 123.22, 125.23, 125.27, 126.34, 130.07, 131.02, 131.16, 132.25, 133.66, 133.83, 141.02, 160.78, 164.74, 169.84. Anal. Calcd for $C_{13}H_8FNO_2S$: C, 59.76; H, 3.09; N, 5.36; S, 12.27. Found: C, 59.78; H, 3.03; N, 5.40; S, 12.33.

3-(3-Methylphenyl)-1,2-benzisothiazole 1,1-Dioxide (IIIe). The Grignard reaction was carried out as for the general procedure using saccharin (1.83 g, 10 mmol) and 3-methylphenylmagnesium chloride (22 mL, 22 mmol), followed by acidic workup and extraction with dichloromethane (4×30 mL). Evaporation of the solvent gave a residue, which was purified by column chromatography (4:1 hexanes-ethyl acetate) to give the tertiary alcohol intermediate as a white solid. The solid was dissolved in toluene, p-toluenesulfonic acid monohydrate (76 mg, 0.4 mmol) was added, and the solution was refluxed for 2 h with removal of water by a Dean-Stark trap. Evaporation of toluene gave a solid that, upon column chromatography, yielded the pure product (yield 1.98 g, 77%): mp 136–137° C. (ethyl acetate-hexanes). $^1$H NMR (CDCl$_3$): δ 2.48 (s, 3H, CH$_3$), 7.49–8.03 (8H, m, ArH); $^{13}$C NM (CDCl$_3$): δ 21.40, 123.00, 126.64, 129.01, 129.95, 130.36, 130.64, 133.32, 133.59, 134.22, 139.33, 141.09, 171.19. Anal. Calcd for C$_{14}$H$_{11}$NO$_2$S: C, 65.35; H, 4.31; N, 5.44; S, 12.46. Found: C, 65.40; H, 4.31; N, 5.36; S, 12.40.

3-(2-Methylphenyl)-1,2-benzisothiazole 1,1-Dioxide (IIIf). Yield: 75%; mp 125–126° C. (ethyl acetate-hexanes); lit.[1] mp 118° C. $^1$H NMR (CDCl$_3$): δ 2.48 (s, 3H, CH$_3$), 7.35–8.03 (8H, m, ArH); $^{13}$C NMR (CDCl3): δ 20.17, 122.79, 125.91, 126.57, 128.92, 129.23, 131.62, 131.83, 133.37, 133.69, 137.86, 140.29, 172.11.

Asymmetric Transfer Hydrogenation: Synthesis of Sultam Using the Noyori Catalyst (+)-(S)-3-Aryl-2,3-Dihydrobenzo[d]isothiazoline 1,1-Dioxides (IV). The in situ catalytic method is essentially that of Noyori and co-workers[3] as adapted for sultams by Ahn and co-workers (ref. 3) [RuCl$_2$(η$^6$-p-cymene)]$_2$ (15.3 mg, 0.025 mmol), (1S,2S)-N-(p-toluenesufonyl)-1,2-diphenylenediamine [(S,S)-TsDPEN][5] (18.3 mg, 0.05 mmol) and triethylamine (3 mL) were added to a flask. The mixture was heated and stirred at 80° C. under nitrogen for 1 h, then cooled to room temperature. A solution of the N-sulfonylimine (5 mmol) in 20 mL of dichloromethane was added to the mixture. Following the methods of Wagner (ref. 10) and Narita et al., (ref. 11) an azeotropic mixture of 5:2 formic acid-triethylamine (2.5 mL) was added at the specified reaction temperature. The solution was stirred at that temperature until the starting material disappeared as determined by TLC. Na$_2$CO$_3$ was added to render the solution basic, and it was then extracted with ethyl acetate. The organic phase was washed with brine and dried over MgSO$_4$. Evaporation of solvents gave the crude product that was purified by column chromatography (4:1 hexanes-ethyl acetate). Recrystallization from ethyl acetate-hexanes gave the pure (+)-(S)-enantiomer.

Compounds IVa–f were similarly prepared.

(+)-(S)-3-Phenyl-2,3-dihydrobenzo[d]isothiazoline 1,1-Dioxide (IVa). The reaction was carried out at 28° C. for 3 h. Yield: 97%; ee 68% by HPLC: $t_R$ 37.93 min, (S)-isomer; $t_R$ 44.75 min, (R)-isomer; (85:15 hexanes-2-propanol; flow rate, 3 mL/min); mp 139° C. (chloroform-hexanes); $[α]_D^{20}$+103° (c, 0.34, CHCl$_3$). $^1$H NMR(CDCl$_3$): δ 5.12 (1H, br, NH), 5.71 (1H, d, J=3.8 Hz, CHN), 7.11–7.83 (9H, m, ArH); $^{13}$C NMR (CDCl$_3$): δ 61.32 (C—N), 121.08, 121.54, 125.34, 127.55, 128.03, 128.21, 129.43, 133.26, 134.74, 138.67, 139.77 (Ar). Anal. Calcd for C$_{13}$H$_{11}$NO$_2$S: C, 63.66; H, 4.52; N, 5.61; S, 13.07. Found: C, 63.54; H, 4.56; N 5.61; S. 13.14.

(+)-(S)-3-(3-Chlorophenyl)-2,3-dihydrobenzo[d]isothiazoline 1,1-Dioxide (IVb). The reaction was carried out at 28° C. for 3 h. Yield: 96%; ee 69% by HPLC: $t_R$ 19.00 min, (S)-isomer; $t_R$ 23.64 min, (R)-isomer; (75:25 hexanes-2-propanol; flow rate, 3 mL/min); mp 162° C. (ethyl acetate-hexanes); lit.[9] mp 137–138° C. for the racemic compound; $[α]_D^{20}$+121° (c 0.29, CHCl$_3$); $^1$H NMR (CDCl$_3$): δ 5.25 (1H, br, NH), 5.70 (1H, d, J=4.1 Hz, CHN), 7.13–7.84 (8H, m, ArH); $^{13}$C NMR (CDCl$_3$): δ 60.54 (C—N), 121.21, 125.25, 125.67, 127.58, 129.17, 129.70, 130.49, 133.44, 133.47, 135.02, 138.70, 140.80 (Ar). Anal. Calcd for C$_{13}$H$_{10}$ClNO$_2$S: C, 55.82; H, 3.60; Cl, 12.67; N, 5.01; S, 11.46. Found: C, 55.70; H, 3.56; Cl, 12.62; N, 4.94; S, 11.39.

(+)-(S)-3-(3-Bromophenyl)-2,3-dihydrobenzo[d]isothiazoline 1,1-Dioxide (IVc). The reaction was carried out at 20° C. for 7 h. Yield: 94%; ee 92% by HPLC of the N-methylated product: $t_R$ 19.34 min, (S)-isomer; $t_R$ 25.59 min, (R)-isomer; (9:1 hexanes-2-propanol; flow rate, 3 mL/min); mp 163° C. (ethyl acetate-hexanes); $[α]_D^{20}$+109° (c 0.48, CHCl$_3$); $^1$H NMR (CDCl$_3$): δ 5.09 (1H, br, NH), 5.69 (1H, d, J=4.7 Hz, CHN), 7.13–7.86 (8H, m, ArH); $^{13}$C NMR (CDCl$_3$): δ 60.55 (C—N), 121.28, 123.17, 125.25, 126.18, 129.77, 130.54, 130.83, 132.25, 133.50, 134.61, 138.67, 140.95 (Ar). Anal. Calcd for C$_{13}$H$_{10}$BrNO$_2$S: C, 48.16; H, 3.11; Br, 24.65; N, 4.32; S, 9.89. Found: C, 48.32; H, 3.06; Br, 24.75; N, 4.16; S,10.00.

(+)-3-(3-Fluorophenyl)-2,3-dihydrobenzo[d]isothiazoline 1,1-Dioxide (IVd). The reaction was carried out at 28° C. for 3 h. Yield: 94%; ee 75% by HPLC: $t_R$ 14.82 min, (S)-isomer; $t_R$ 24.01, min, (R)-isomer; (75:25 hexanes-2-propanol; flow rate, 3 mL/min); mp 148° C. (ethyl acetate-hexanes); $[α]_D^{20}$130° (c 0.11, CHCl$_3$). $^1$H NMR (CDCl$_3$): δ 5.07 (1H, br, NH), 5.73 (1H, d, J=4.2 Hz, CHN), 7.07–7.86 (8H, m, ArH); $^{13}$C NMR (CDCl$_3$): δ 60.52, 114.23, 114.58, 115.72, 116.08, 121.12, 123.07, 125.21, 129.62, 130.68, 130.82, 133.38, 134.37, 138.98, 141.23, 141.34, 161.01, 164.95 (Ar). Anal. Calcd for Cl$_3$H$_{10}$FNO$_2$S: C, 59.31; H, 3.83; N, 5.32; S, 12.18. Found: C, 59.31; H, 3.76; N, 5.25; S, 12.27.

(+)-3-(3-Methylphenyl)-2,3-dihydrobenzo[d]isothiazoline 1,1-Dioxide (IVe). The reaction was carried out at 28° C. for 3 h. Yield: 93%; ee 74% by HPLC of the N-methylated product: $t_R$ 14.53 min, (S)-isomer; $t_R$ 18.99 min, (R)-isomer; (9:1 hexanes-2-propanol; flow rate, 3 mL/min); mp 158–159° C. (ethyl acetate-hexanes); $[α]_D^{20}$+122° (c 0.09, CHCl$_3$). $^1$H NMR (CDCl$_3$): δ 2.34 (3H, s, CH$_3$), 4.93 (1H, br, NH), 5.67 (1H, d, J =4.0 Hz, CHN), 7.12–7.85 (8H, m, ArH); $^{13}$C NMR (CDCl$_3$): δ 21.36, 61.41, 121.11, 124.71,125.37, 126.10, 129.13, 129.43, 129.92, 133.29, 134.86, 138.53, 139.22, 139.92 (Ar). Anal. Calcd for C$_{14}$H$_{13}$NO$_2$S: C, 64.84; H, 5.05; N, 5.40; S, 12.36. Found: C, 64.74; H, 5.05; N, 5.32; S, 12.50.

(+)-3-(2-Methylphenyl)-2,3-dihydrobenzo[d]isothiazoline 1,1-Dioxide (IVf). The reaction was carried out at 28° C. for 38 h. Yield: 89%; ee 65% by HPLC: $t_R$ 15.27 min, (+)-isomer; $t_R$ 18.66 min, (−)-isomer; (75:25 hexanes-2-propanol; flow rate, 3 mL/min); mp 109–111 ° C. (ethyl acetate- hexanes); $[α]_D^{20}$+14.6° (c 0.37, CHCl$_3$). $^1$H NMR (CDCl$_3$): δ 2.45 (3H, s, CH$_3$), 4.80 (1H, br, NH), 6.01 (1H, d, J=4.5 Hz, CHN), 7.10–7.87 (8H, m, ArH); $^{13}$C NMR (CDCl$_3$): δ 19.35, 56.27, 121.27, 125.19, 127.06, 128.05, 129.10, 129.43, 131.25, 133.29, 135.71, 136.13, 136.74, 140.08 (Ar). Anal. Calcd for C$_{14}$H$_{13}$NO$_2$S: C, 64.84; H, 5.05; N, 5.40; S, 12.10. Found: C, 64.62; H, 5.23; N, 5.20; S, 12.10.

Asymmetric Transfer Hydrogenation: Synthesis of Optically Pure Sultam Using the Catalyst of Invention Method 1: Reduction using Preformed Catalyst. To a solution of the appropriate sulfonylimine (4 mmol) and the preformed catalyst (0.02 mmol) in dry dichloromethane (20 mL) was added at 20° C., under nitrogen, an azeotropic mixture of 5:2 formic acid-triethylamine (2 mL). The mixture was stirred until the substrate disappeared as determined by TLC. $Na_2CO_3$ (0.5 M) was added to render the mixture basic, and the mixture was extracted with dichloromethane. The combined organic phase was washed with brine, dried over $MgSO_4$, and concentrated to give a crude product that was purified by column chromatography on silica gel.

Method 2: Reduction using Catalyst Generated in situ. A solution of $[RhCl_2Cp^*]_2$ (0.01 mmol), (R,R)-TsDPEN (0.022 mmol, 1.1 equiv) and triethylamine (0.048 mmol, 2.4 equiv) in dry dichloromethane (2 mL) was stirred for 20 min under nitrogen at 20° C. A solution of the appropriate sulfonylimine (4 mmol) in dichloromethane (18 mL) and an azeotropic mixture of 5:2 formic acid-triethylamine (2 mL) were added to the mixture with continued stirring. The mixture was stirred until the substrate disappeared as determined by TLC. Workup and purification of the product were carried out as described in Method 1.

(+)-(S)-3-Phenyl-2,3-dihydrobenzo[d]isothiazoline 1,1-Dioxide (IVa). The reaction was carried out at 20° C. for 40 min using either Method 1 or Method 2: yield, 95%; ee 86% by HPLC: $t_R$ 34.28 min, (S)-isomer; $t_R$ 42.02 min, (R)-isomer; (85:15 hexanes-2-propanol; flow rate, 3 mL/min); mp 139° C. (chloroform-hexanes), $[\alpha]_D^{20}$+103° (c 0.34, $CHCl_3$).

(+)-(S)-3-(3-Chlorophenyl)-2,3-dihydrobenzo[d]isothiazoline 1,1-Dioxide (IVb). Using Method 1, the reaction was carried out at 20° C. for 30 min: yield, 96%; ee 81% by HPLC: $t_R$ 19.58 min, (S)-isomer; $t_R$ 23.35 min, (R)-isomer; (75:25 hexanes-2-propanol; flow rate, 3 mL/min); mp 162° C. (ethyl acetate-hexanes); $[\alpha]_D^{20}$+121° (c 0.29, $CHCl_3$).

(+)-3-(3-Fluorophenyl)-2,3-dihydrobenzo[d]isothiazoline 1,1-Dioxide (IVd). Using Method 1, the reaction was carried out at 20° C. for 25 min: yield, 96%; ee 85% by HPLC: $t_R$ 15.01 min, (+)-isomer; $t_R$ 24.58 min, (-)-isomer); (75:25 hexanes-2-propanol; flow rate, 3 mL/min); mp 148° C. (ethyl acetate-hexanes); $[\alpha]_D^{20}$+130° (c 0.12, $CHCl_3$).

(+)-3-(3-Methylphenyl)-2,3-dihydrobenzo[d]isothiazoline 1,1-Dioxide (IVe). Using Method 1, the reaction was carried out at 20° C. for 10 min: yield, 94%; ee 95% by HPLC of the methylation product: $t_R$ 15.06 min, (+)-isomer; $t_R$ 19.69 min, (-)-isomer; (9:1 hexanes-2-propanol; flow rate, 3 mL/min); mp 158–159° C. (ethyl acetate-hexanes); $[\alpha]_D^{20}$+122° (c 0.1, $CHCl_3$).

Methylation of the Sultam Nitrogen Atom (+)-(S)-3-Aryl-2-methyl-2,3-dihydrobenzo[d]isothiazole 1,1-Dioxide (V). Method 3 via the Mitsunobu reaction. Over a period of 10 min, at room temperature, with stirring, diethyl diazocarboxylate (DEAD, 3 mmol) was added to a solution of compound IV (2.0 mmol), $Ph_3P$ (3.0 mmol), and MeOH (3.0 mmol) in 13.5 mL of THF that was maintained under nitrogen. The mixture was stirred at room temperature for another 15 min. Compound IV was shown to disappear as determined by TLC. Evaporation of the solvents gave a solid mixture that was purified by column chromatography to afford the purified product. Recrystallization from ethyl acetate-hexanes gave the crystalline product.

Method 4 (direct alkylation). A mixture of compound IV (2.0 mmol), $Cs_2CO_3$ (2.6 mmol), and DMF (20 mL) was stirred at room temperature for 30 min. MeI (2.6 mmol) was added, and the reaction mixture was stirred at room temperature for another 1 h, then poured into 80 g of ice water. The white solid was filtered off and dried. Recrystallization from ethyl acetate-hexanes gave the pure product. (+)-(S)-2-Methyl-3-phenyl-2,3-dihydrobenzo[d]isothiazole 1,1-Dioxide (Va). By Method 3, the product was obtained after column chromatography (5:1 hexanesethyl acetate): yield, 94%; ee >99% by HPLC: $t_R$ 16.72 min, (S)-isomer; (9:1 hexanes-2-propanol; flow rate, 3 mL/min); mp 156–157° C. (chloroform-hexanes); lit.[10] mp 135–136° C. for the racemic compound; $[\alpha]_D^{20}$+152° (c 0.26, $CHCl_3$). $^1H$ NMR ($CDCl_3$): δ 2.78 (3H, s, $CH_3$), 5.19 (1H, s, CHN), 7.02–7.87 (9H, m, ArH) $^{13}C$ NMR ($CDCl_3$): δ 27.40 ($CH_3$), 66.99 (C—N), 121.10, 124.98, 128.13, 129.16, 129.31, 132.93, 134.04, 136.65, 136.38 (Ar).

(+)-(S)-3-(3-Chlorophenyl)-2-methyl-2,3-dihydrobenzo[d]isothiazole 1,1-Dioxide (Vb). By Method 3, the pure product was obtained after column chromatography (5:1 hexanes-ethyl acetate): yield, 96%; ee>99% by HPLC (9:1 hexanes-2-propanol; flow rate, 3 mL/min; $t_R$ 18.72 min, (S)-isomer); mp 164° C. (ethyl acetate-hexanes); $[\alpha]_D^{20}$+166° (c 0.26, $CHCl_3$); $^1H$ NMR ($CDCl_3$): δ 2.79 (3H, s, $CH_3$), 5.16 (1H, s, CHN), 7.03–7.88 (8H, m, ArH); $^{13}C$ NMR ($CDCl_3$): δ 27.60 ($CH_3$), 66.40 (C—N), 121.27, 124.67, 126.30, 128.11, 129.46, 129.59, 130.50, 133.13, 133.99, 135.20, 137.56, 138.64 (Ar). Anal. Calcd for $C_{14}H_{12}ClNO_2S$: C, 57.24; H, 4.12; Cl, 12.07; N, 4.77; S, 10.91. Found: C, 57.28; H, 4.12; Cl, 12.00; N, 4.78; S, 11.01. Compound Vb was definitively characterized as the (S)-isomer by single-crystal X-ray crystallography.

(+)-(S)-3-(3-Bromophenyl)-2-methyl-2,3-dihydrobenzo[d]isothiazole 1,1-Dioxide (Vc). The product was obtained by Method 4: yield, 91%; ee>99% by HPLC: $t_R$ 19.34 min, (S)-isomer; (9:1 hexanes-2-propanol; flow rate, 3 mL/min); mp 157° C. (ethyl acetate-hexanes); $[\alpha]_D^{20}$+140° (c 0.41, $CHCl_3$); $^1H$ NMR ($CDCl_3$): δ 2.77 (3H, s, $CH_3$), 5.14 (1H, s,CHN), 7.02–7.87 (8H, m, ArH); $^{13}C$ NMR ($CDCl_3$): δ 27.61 ($CH_3$), 66.35 (C—N), 121.25, 123.26, 124.70, 126.77, 129.59, 130.77, 131.00, 132.40, 133.13, 134.00, 137.56, 139.09 (Ar). Anal. Calcd for $C_{14}H_{12}BrNO_2S$: C, 49.72; H, 3.58; Br, 23.62; N, 4.14; S, 9.48. Found: C, 49.81; H, 3.54; Br, 23.52; N, 4.10; S, 9.43. Compound Vc was definitively characterized as the (S)-isomer by single-crystal X-ray crystallography.

(+)-3-(3-Fluorophenyl)-2-methyl-2,3-dihydrobenzo[d]isothiazole 1,1-Dioxide (Vd). The product was obtained by Method 4: yield, 95%;>99%ee by HPLC: $t_R$ 17.91 min, (+)-isomer; (9:1 hexanes-2-propanol, flowrate, 3 mL/min); mp 147° C. (ethylacetate-hexanes); $[\alpha]_D^{20}$+153° (c 0.27, $CHCl_3$). $^1H$ NMR ($CDCl_3$): δ 2.80 (3H, s, $CH_3$), 5.19 (1H, s, CHN), 7.04–7.88 (8H, m, ArH); $^{13}C$ NMR ($CDCl_3$): δ 27.55, 66.41, 114.75, 115.09, 116.12, 116.46, 121.26, 123.80, 124.85, 129.56, 130.74, 130.86, 133.08, 133.98, 137.62, 139.27, 139.37 (Ar). Anal. Calcd for $C_{14}H_{12}FNO_2S$: C, 60.64; H, 4.36; N, 5.05; S, 11.56. Found: C, 60.54; H, 4.32; N, 5.01; S, 11.48.

(+)-2-Methyl-3-(3-methylphenyl)-2,3-dihydrobenzo[d]isothiazole 1,1-Dioxide (Ve). The product was obtained by method 4: yield, 93%; ee>99% by HPLC: $t_R$ 15.06 min, (+)-isomer; (9:1 hexanes-2-propanol, flow rate, 3 mL/min); mp 154° C. (ethyl acetate-hexanes); $[\alpha]_D^{20}$+149° (c 0.14, $CHCl_3$). $^1H$ NMR ($CDCl_3$): δ 2.35 (3H, s, $CH_3$), 2.78 (3H, s, $CH_3$), 5.15 (1H, s, CHN), 7.03–7.87 (8H, m, ArH); $^{13}C$ NMR ($CDCl_3$): δ 21.38, 27.41, 67.00, 121.06, 125.00, 125.34, 128.55, 128.97, 129.25, 129.94, 132.92, 134.01, 136.53, 138.46, 139.06 (Ar). Anal. for Calcd for $C_{15}H_{15}NO_2S$: C, 65.91; H, 5.53; N, 5.12; S, 11.73. Found: C, 65.93; H, 5.43; N, 5.10; S, 11.75.

(+)-2-Methyl-3-(2-methylphenyl)-2,3-dihydrobenzo[d]isothiazole 1,1-Dioxide (Vf). By method 4, crude IVf was converted to Vf: yield, 92%. After recrystallization, the pure (+)-isomer was obtained in >99% ee as determined by HPLC: $t_R$ 14.00 min, (+)-isomer; (9:1 hexanes-2-propanol; flow rate, 3 mL/min); mp 152° C. (ethyl acetate-hexanes); $[\alpha]_D^{20}$+155° (c 0.17, $CHCl_3$). $^1H$ NMR ($CDCl_3$): δ 2.32 (3H, s, $CH_3$), 2.76 (3H, s, $CH_3$), 5.45 (1H, s, CHN), 6.97–7.89 (8H, m, ArH); $^{13}C$ NMR ($CDCl_3$): δ 19.25, 27.37, 64.45, 121.26, 124.52, 126.89, 128.97, 129.22, 131.43, 133.01, 133.99, 134.34, 137.05, 138.38 (Ar). Anal. Calcd for $C_{15}H_{15}NO_2S$: C, 65.91; H, 5.53; N, 5.12; S, 11.73. Found: C, 65.91; H, 5.41; N 5.08; S, 11.65.

Preparation of 3-(3-Iodophenyl)sultam (+)-(S)-2-Methyl-3-(3-tributylstannylphenyl)-2,3-dihydrobenzo[d]isothiazole 1,1-Dioxide (IX).[12] (+)-(S)-2-Methyl-3-(3-bromophenyl)-2,3-dihydrobenzo[d]isothiazole 1,1-dioxide (Vc) (169 mg, 0.5 mmol) and $Pd(PPh_3)_4$ (8.67 mg, 0.0075 mmol) were dissolved in degassed toluene (5 mL, degassed by applying at room temperature vacuum from a water aspirator, ~40 torr), and $(Bu_3Sn)_2$ (580 mg, 1.0 mmol) was dropped into the solution. Degassing was continued for another 10 min, and the mixture was then refluxed for 4 h. Evaporation of the solvent gave an oil that was purified by column chromatography (9:1 hexanes-ethyl acetate) to afford the product as an oil: 162 mg (59%). $^1H$ NMR ($CDCl_3$): δ 0.84 1.62 (27H, m, 3×n-Bu), 2.78 (3H, s, $CH_3$), 5.15 (1H, s, CHN), 7.01–7.87 (8H, m, ArH); $^{13}C$ NMR ($CDCl_3$): δ 9.65, 9.95, 13.65, 26.82, 27.26, 29.05, 30.61 (n-Bu), 27.45 ($CH_3$), 67.17 (C—N), 121.06, 124.98, 127.55, 128.62, 129.16, 132.80, 134.17, 135.74, 136.25, 137.20, 138.63, 143.39 (Ar).

(+)-(S)-2-Methyl-3-(3-iodophenyl)-2,3-dihydrobenzo[d] isothiazole 1,1-Dioxide (X). To a degassed solution of compound IX (137 mg, 0.25 mmol) in dichloromethane (20 mL) was added iodine (381 mg, 1.5 mmol), and the reaction mixture was stirred under nitrogen at room temperature overnight. The reaction was quenched with 1% aq $Na_2S_2O_3$. The aqueous layer was extracted with dichloromethane (2×20 mL), and the combined organic phase was dried over $MgSO_4$ and concentrated to dryness. Column chromatography (4:1 hexanes-ethyl acetate) gave the pure product X (65 mg, 68%); ee>99% by HPLC: $t_R$ 21.81 min, (S)-isomer); (9:1 hexanes-2-propanol; flow rate, 3 mL/min); mp 156° C. (ethyl acetate-hexanes); $[\alpha]_D^{20}$+126° (c 0.26, $CHCl_3$). $^1H$ NMR ($CDCl_3$): δ 2.77 (3H, s, $CH_3$), 5.10 (1H, s, CHN), 7.02–7.88 (8H, m, ArH); $^{13}C$ NMR ($CDCl_3$): δ 27.63 ($CH_3$), 66.23 (C—N), 94.86 (C-I), 121.27, 124.91, 127.38, 129.56, 130.91, 133.13, 133.99, 136.66, 137.59, 138.36, 139.06 (Ar). Anal. Calcd for $C_{14}H_{12}INO_2S$: C, 43.65; H, 3.14; I, 32.94; N, 3.64; S 8.32. Found: C, 43.70; H, 3.11; I, 32.87; N, 3.59; S, 8.28.

BIOLOGICAL ACTIVITIES OF THE COMPOUNDS OF THE INVENTION

In studies in conjunction with the invention, it was found that the anti-HIV activity of the compounds of the invention varied in an unforeseeable manner depending on the nature of the individual substituents, on the size and bulkiness of the substituents, on their polarity, the ring on which and at which position the substituent(s) is linked, whether or not the nitrogen is substituted, and by what substituent, whether there was a substituent on the stereogenic center at C-3, and in what position (ortho-, meta-, or para-) the substituents were linked on the C ring of the sultams. From the data of anti-HIV structure-activity relationships, it was thus observed that both steric and electronic factors played an important role. These studies further suggested that the most active sites for substitutions to be positioned is on the nitrogen of the B ring and the ortho- or meta-position of the C ring.

Antiviral/anti-HIV Activity of the Sultams

A primary objective of the invention was to find compounds that exhibit high activity as antiviral, especially anti-HIV activity. Indeed, as described, the sultams of the invention are highly effective in that respect, whether as racemates, or when resolved in their respective (+)-enantiomers. The sultams of the invention have biological activity that make them interesting candidates for biological applications other than (or in addition to) anti-HIV drugs. It is not excluded that they may have fungicidal or insecticidal properties or the ability to control other undesirable microorganisms, which is of interest in agricultural applications. Veterinary applications to control animal infections are also contemplated. The sultams of the invention are especially useful to inhibit the growth or replication of a virus in animals, especially mammals. Examples of mammals include humans, primates, bovines, ovines, porcines, felines, canines, elephantidae, etc. Examples of viruses include but are not limited to HIV-1, HIV-2, herpes simplex virus (types 1 and 2), varicella zoster virus, cytomegalovirus, papilloma virus, HTLV-1, HTLV-2, feline leukemia virus, avian sarcoma viruses such as rous sarcoma virus, hepatitis types A–E, influenza virus, measles, mumps and rubella viruses. In a presently preferred use, the compounds of the invention are used to treat a human at risk, exposed or infected (i.e., in need of such treatment) with the human immunodeficiency virus, either prophylactically or therapeutically.

The sultams of the invention are accordingly particularly useful in the treatment of infection by the human immunodeficiency virus and also in the treatment of consequent pathological conditions associated with AIDS. Treating AIDS is defined as including, but not limited to, treating a wide range of states of HIV infection: AIDS, ARC (AIDS related complex), both symptomatic and asymptomatic, and actual or potential exposure to HIV. For example, the sultams of the invention are useful in treating infection by HIV after suspected exposure to HIV by, for example, blood transfusion, exposure to patient blood during surgery, or an accidental hypodermic needle stick. The sultams could be used in the prevention/treatment of neonatal HIV infection that arises from mother-to-infant transmission. Nevirapine has recently been resurrected and shown to be very effective and inexpensive for treatment of neonatal HIV. The compounds of the invention are equipotent and in some cases, more potent than nevirapine and show great potential for competing with nevirapine for the neonatal market.

An advantage to the compounds of the invention is that they retain the ability to inhibit HIV RT mutants that are resistant to TiBO and other compounds known to inhibit RT. This is advantageous over the current AIDS drug therapy, where biological resistance tends to develop to nucleoside or non-nucleoside analogues used in the inhibition of RT.

As described herein above, the compounds of the invention are non-nucleoside reverse transcriptase inhibitors (NNRTI), also referred to as "second-site" RT inhibitors. The compounds of the invention influence the metabolic pathway by allosteric regulatory site and influence the RT catalytic site; hence the sultams are considered inhibitory modulators specific and binding to the allosteric site. This site is believed to be found on the regulatory subunit of the RT enzyme, which is in communication with the catalytic subunit of the RT to conform or fit to the regulatory site of the enzyme with an affinity heretofore not yet observed, of an order of magnitude be in the range of $10^{-6}$ to $10^{-9}$ M for inhibition of 50–100% of the enzyme's activity.

The sultams of the invention may be assayed for antiviral activity in accordance with published protocols. They include, but are not limited to, cell count, cytopathic effect, dish-colony formation, microtiter-growth inhibition and thymidine incorporation.

In addition, the compounds of the present invention can be assayed for their ability to inhibit HIV infection via an infectivity assay. The infectivity assay comprises infection of T-lymphocytes or macrocytes/macrophages with either HIV-1 or HIV-2. At six or more days post-infection, measurement of particle-associated reverse transcriptase activity and/or p24 antigen levels can be determined (see, for example, Clapham et al. (1990) Nature, 337:368–370 or McDougal et al. (1985) J. Immun. Meth. 76:171–183. In addition, the focal infectivity assay (FIA) can be used to assay the susceptibility of HIV to antiviral agents (see, e.g., Pincus et al. (1991) Bio. Techniques 10:336–342. Furthermore, the levels of antiviral "activity" of the compounds of the present invention can be rapidly determined in a series of interrelated assays via a semiautomated multiparameter approach as disclosed by Gulakowski et al. (1991) J. Virol. Meth. 33:87–100, which is incorporated herein by reference.

The sultams of the invention were tested in accordance with the National Cancer Institute Protocol, Weislow, O. W., et al. (1989) J. Natl. Cancer Inst. 81:577–586, which is incorporated herein by reference. The protocol is also described in U.S. Pat. No. 5,843,990.

The anti-HIV activity of compounds of the invention illustrated by the formula V shown above, is reported below.

Table III illustrates anti-HIV-1 activities of compounds of the invention, the substituents (shown in formula V).

TABLE III

| No. | $R^A$ | $R^N$ | $R^C$ | Config. | Opt. Rot. (deg.) | mp (deg. C.) | $EC_{50}$ (uM) | $IC_{50}$ (uM) | $TL_{50}$ | Act.[1] |
|---|---|---|---|---|---|---|---|---|---|---|
| 5. | H | Me | H | (+)-(S) | +147 | 156–157 | 0.471 | >316 | >674 | A |
| 6. | H | Me | H | (−)-(R) | −148 | 156–157 | — | >316 | — | I |
| 7. | H | Me | 3-Me | (+)-(S) | +149 | 154 | 0.037 | >2.0 | >54 | A |
| 9. | H | Me | 3-Br | (+)-(S) | +140 | 157 | 0.074 | 101 | 136.5 | A |
| 11. | H | Me | 3-Cl | (+)-(S) | +166 | 164 | 0.086 | >2 | >31 | A |
| 12. | H | Me | 3-Cl | (−)-(R) | −150 | 160 | 5.28 | 26.8 | 5.06 | M |
| 13. | H | Me | 3-F | (+)-(S) | +153 | 147 | 0.179 | 147 | 538 | A |
| 15. | H | Me | 3-I | (+)-(S) | +126 | 156 | 0.076 | 62.4 | 817 | A |
| 18. | H | Me | 2-Me | (+)-(S) | +155 | 152 | 4.68 | 123 | 26.3 | M |
| 20. | H | Me | 4-Me | (+)-(S) | +131 | 126–129 | 1.53 | 138 | 90.4 | A |
| 21. | H | Me | 4-Me | (−)-(R) | −127 | 126–127 | — | — | — | I |
| 30. | H | Me | 4-OMe | (+)-(S) | +119 | 166–167 | — | >200 | — | I |
| 31. | H | Me | 4-OMe | (−)-(R) | −120 | 166 | — | >200 | — | I |
| 50. | H | Me | 3-Et | (+)-(S) | +133 | 106–107 | 0.12 | 35 | 42.8 | A |
| 51. | H | Me | 3-inyl | (+)-(S) | +106 | 113–114 | 0.90 | 3.07 | 4.35 | M |

Activities are defined as per the NCI protocol: A = "active"; M = "moderately active"; I = "inactive".

Pharmaceutical Compositions

Pharmaceutical compositions that comprise one or more compounds of the invention may be formulated, as is well known in the prior art, such as by reference to known compilations as Remington's Pharmaceutical Sciences, Mack Publishing Co., Easton, Pa., USA. The dosage ranges for administration of the compounds of the invention are those needed to produce the desired affect without undue toxicity, whereby symptoms of infection are ameliorated.

The pharmaceutical composition may contain other pharmabiologically active compounds in a mixture with the compounds of the invention, to treat (therapeutically or prophylactically) acquired immunodeficiency syndrome (AIDS). For example, other active compounds may include, but are not limited to, other antiviral compounds (e.g., AZT, ddC, TiBO derivatives, acyclovir, alpha-interferon), immunostimulants (e.g., various interleukins and cytokines), immunomodulators and antibiotics (e.g., antibacterial, antifungal, anti-pneumocystis agents), even when these do not show potent activity in the NCI Weislow protocol.

In addition, the compounds of the invention, like HIV reverse transcriptases, are useful as tools and/or reagents to study inhibition of retroviral reverse transcriptases. Hence, the compounds are useful as a SAR (structure-activity relationships) tools to study, select and/or design other molecules to inhibit HIV. The active compounds described in this text are potentially useful in combination therapy with one or more of the compounds to provide an attractive regimen to halt proliferation of HIV under clinical conditions. Such agents include, but are not restricted to, inhibitors of HIV reverse transcriptase, e.g., AZT (zidovudine, Retrovir.RTM.), ddI (dideoxyinosine, didanosine, Videx.RTM.), d4T (dideoxydidehydrothymidine, stavudine), ddC (dideoxycytidine, zalcitabine), and nevirapine, among others. Combination regimens with HIV protease inhibitors might include, but are not restricted to, e.g., ritonavir (Norvir.RTM.) or saquinavir mesylate (Invirase.RTM.), among other drugs.

The preferred route of administration is oral, although other routes of administration are acceptable. The compounds may be mixed with inert materials for pharmaceutical efficacy as is known in the art. The compounds may be formulated in aqueous solution for intravenous (i.v.), intraperitoneal (i.p.), or subcutaneous (s.c.) administration. Topical applications include mixtures of the compounds with oils or fatty acid esters or as components of skin patches that are capable of delivering the drugs across the dermal layer.

Aqueous solutions, or solutions in suitable carriers, may be administered intranasally.

The compounds of the invention readily lend themselves to being made part of what are called "inclusion compounds", such as with cyclodextrins and other suitable substances.

All publications referenced herein are hereby incorporated by reference in their entirety. The invention is not limited to the embodiments described herein, but encompasses all modifications within the scope of the following claims and equivalent thereof.

We claim:

1. A process of preparing a sultam of the formula (IV)

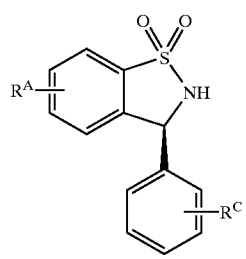

IV wherein $R^A$ is selected from the group consisting of hydrogen, a linear- or branched-chain hydrocarbon (saturated or unsaturated), and a halogen; where $R^C$ is selected from the group consisting of a hydrogen, 1–5 halogens, a linear or branched hydrocarbon, hydroxyl, alkoxy, $CF_3$, 1–2 alkyl groups, phenyl, and amide comprising:

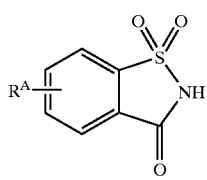

I (a) reacting compound I, wherein $R^A$ is selected from the group consisting of hydrogen, a linear- or branched-chain hydrocarbon (saturated or unsaturated), and a halogen, with an aryl Grignard reagent in an aprotic solvent, thereby forming a sulfonylimine;

(b) performing an asymmetric transfer hydrogenation of said sulfonylimine by heating a precatalyst solution comprising a $[RuCl_2(\eta^6p\text{-cymene})]_2$ precatalyst, (1S,2S)-N-p-toluenesulfonyl-1,2-diphenylethylenediamine, and triethylamine; and adding to said solution said sulfonylimine and a mixture of formic acid-triethylamine, thereby forming a sultam having an absolute configuration according to formula IV, such that said sultam is an (S) sultam except where $R^C$ is a halogen and in the 2-position.

2. The process of claim 1 wherein said Grignard reagent is phenylmagnesium bromide.

3. The process of claim 1 wherein the Grignard reagent is 3-chlorophenylmagnesium bromide.

4. The process of claim 1 wherein the Grignard reagent is 3-bromophenylmagnesium bromide.

5. The process of claim 1 wherein the Grignard reagent is 3-fluorophenylmagnesium bromide.

6. The process of claim 1 wherein the Grignard reagent is 3-methylphenylmagnesium chloride.

7. The process of claim 1 wherein the Grignard reagent is 3-methylphenylmagnesium bromide.

8. The process of claim 1 wherein the Grignard reagent is an aryl bromide or iodide.

9. A process of preparing a sultam of the formula (IV)

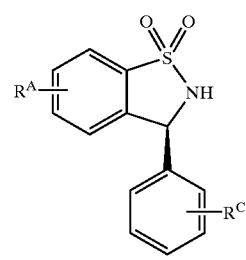

IV wherein $R^A$ is selected from the group consisting of hydrogen, a linear- or branched-chain hydrocarbon (saturated or unsaturated), and a halogen; where $R^C$ is selected from the group consisting of a hydrogen, 1–5 halogens, a linear or branched hydrocarbon, hydroxyl, alkoxy, $CF_3$, 1–2 alkyl groups, phenyl, and amide comprising:

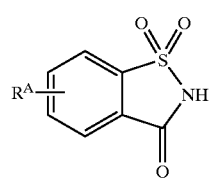

I (a) reacting compound I, wherein $R^A$ is selected from the group consisting of hydrogen, a linear- or branched-chain hydrocarbon(saturated or unsaturated), and a halogen, with an aryl lithium reagent in an aprotic solvent, thereby forming a sulfonylimine;

(b) performing an asymmetric transfer hydrogenation of said sulfonylimine by heating a precatalyst solution comprising a $[RuCl_2(\eta^6p\text{-cymene})]_2$ precatalyst, (1S,2S)-N-p-toluenesulfonyl-1,2-diphenylethylenediamine, and triethylamine; and adding to said solution said sulfonylimine and a mixture of formic acid-triethylamine, thereby forming a sultam having an absolute configuration according to formula IV, such that said sultam is an (S) sultam except where $R^C$ is a halogen and in the 2-position.

10. A process of preparing a sultam of formula IV

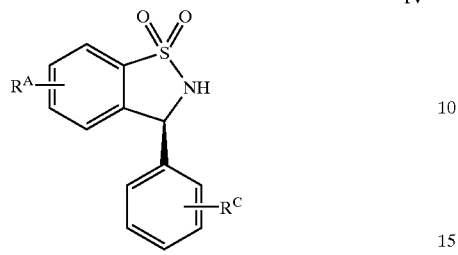

wherein $R^A$ is selected from the group consisting of hydrogen, a linear- or branched-chain hydrocarbon (saturated or unsaturated), and a halogen; where $R^C$ is selected from the group consisting of a hydrogen, 1–5 halogens, a linear or branched hydrocarbon, hydroxyl, alkoxy, $CF_3$, 1–2 alkyl groups, phenyl, and amide comprising:

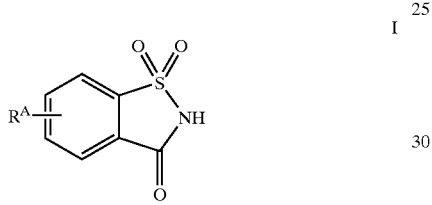

(a) reacting compound I, wherein $R^A$ is selected from the group consisting of hydrogen, a linear- or branched-chain hydrocarbon (saturated or unsaturated), and a halogen, with an aryl Grignard reagent in an aprotic solvent, yielding a sulfonylimine;

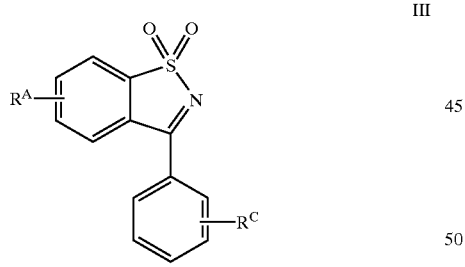

(b) performing an asymmetric transfer hydrogenation comprising adding an (S)-RhClCp*[(1R,2R)-p-TsNCH($C_6H_5$)CH($C_6H_5$)NH$_2$] preformed precatalyst thereby forming a solution of the catalyst and sulfonyl imine III, and as a source of hydrogen a mixture of formic acid-triethylamine, and forming a product wherein the predominant enantiomer is the target enantiomer a sultam having an absolute configuration according to formula IV, such that said sultam is an (S) sultam except where $R^C$ is a halogen and in the 2-position.

11. The process of claim 10 wherein the Grignard reagent is 3-chlorophenylmagnesium bromide.

12. The process of claim 10 wherein the Grignard reagent is 3-fluorophenylmagnesium bromide.

13. The process of claim 10 wherein the Grignard reagent is 3-methylphenylmagnesium chloride.

14. The process of claim 10 wherein the Grignard reagent is 2-methylphenylmagnesium bromide.

15. The process of claim 10 wherein the Grignard reagent is an aryl bromide or iodide.

16. A process of preparing a sultam of formula (IV)

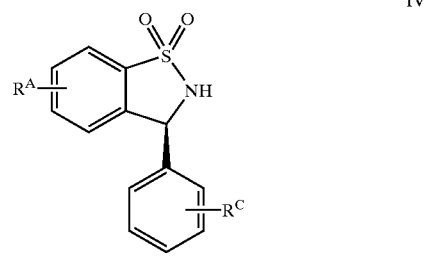

wherein $R^A$ is selected from the group consisting of hydrogen, a linear- or branched-chain hydrocarbon (saturated or unsaturated), and a halogen; where $R^C$ is selected from the group consisting of a hydrogen, 1–5 halogens, a linear or branched hydrocarbon, hydroxyl, alkoxy, $CF_3$, 1–2 alkyl groups, phenyl, and amide comprising:

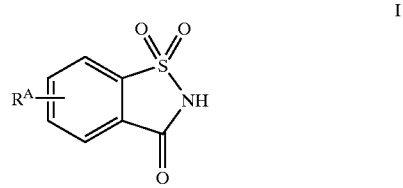

(a) reacting under reactive conditions compound I, wherein $R^A$ is selected from the group consisting of hydrogen, a linear- or branched-chain hydrocarbon (saturated or unsaturated), and a halogen, with an aryl lithium reagent in an aprotic solvent, yielding a sulfonylimine;

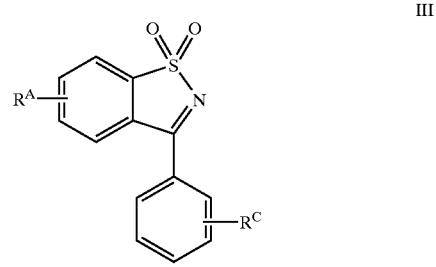

(b) performing an asymmetric transfer hydrogenation comprising adding an (S)-RhClCp*[(1R,2R)-p-TsNCH($C_6H_5$)CH($C_6H_5$)NH$_2$] preformed precatalyst thereby forming a solution of the catalyst and sulfonyl imine III, and as a source of hydrogen a mixture of formic acid-triethylamine, and forming a product wherein the predominant enantiomer is the target enantiomer a sultam having an absolute configuration according to formula IV, such that said sultam is an (S) sultam except where $R^C$ is a halogen and in the 2-position.

17. A process of preparing a sultam of predetermined chirality S by asymmetric catalytic hydrogenation of an imine to secondary amine of structure (IV),

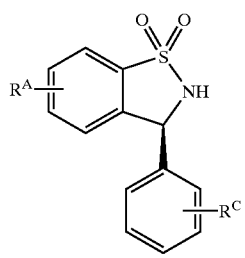

IV wherein $R^A$ is selected from the group consisting of hydrogen, and a methyl group; where $R^C$ is selected from the group consisting of a hydrogen, 1–5 halogens, a linear or branched hydrocarbon, hydroxyl, alkoxy, $CF_3$, 1–2 alkyl groups, phenyl, and amide which comprises:
(a) reacting sulfonylimine with a chiral precatalyst (S)-RhClCp*[(1R,2R)-p-TsNCH($C_6H_5$)CH($C_6H_5$)NH$_2$] of the formula (VIIIa) in a solvent with an azeotropic mixture of 5:2 formic acid-triethylamine,

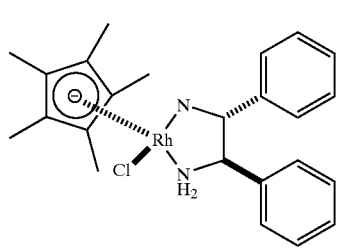

VIIIa thereby forming a product wherein the predominant enantiomer is a sultam having an absolute configuration according to formula IV, such that said sultam is an (S) sultam except where $R^C$ is a halogen and in the 2-position.

18. The process of claim 17 wherein $R^c$ is hydrogen and the solvent is dichloromethane.

19. The process of claim 17 wherein $R^c$ is a 3-chloro group and the solvent is dichloromethane.

20. The process of claim 17 wherein $R^c$ is a 3-fluoro group and the solvent is dichloromethane.

21. The process of claim 17 wherein $R^c$ is a 3-methyl group and the solvent is dichloromethane.

22. The process of claim 17 wherein $R^c$ is a 2-methyl group and the solvent is dichloromethane.

23. The process of claim 17 wherein the molar ratio of substrate/catalyst (S/C) is in the range of over about 100 to 1000 to 1.

24. The process of claim 17 wherein the solvent for the catalyst is a polar solvent.

25. The process of claim 17 wherein the solvent is selected from the group consisting of acetonitrile and dichloromethane.

26. The process of claim 17 wherein the solvent is supercritical carbon dioxide.

27. The process of claim 17 wherein the target enantiomer of predetermined chirality is obtained in an enantiomeric excess of over about 50%.

28. A process of preparing a sultam of predetermined chirality R by asymmetric catalytic hydrogenation of an imine to a secondary amine of formula (IV)

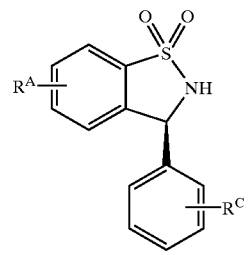

IV wherein $R^A$ is hydrogen, or a methyl group; where $R^c$ is a hydrogen, 1–5 halogens, a linear or branched hydrocarbon, hydroxyl, alkoxy, haloalkyl, 1–2 alkyl groups, phenyl, or amide which comprises reacting sulfonylimine of the formula (III)

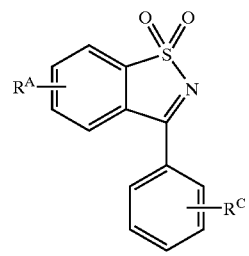

III with a chiral precatalyst (R)-RhClCp*[(1S,2S)-p-TsNCH($C_6H_5$)CH($C_6H_5$)NH$_2$] of the formula (VIIIb)

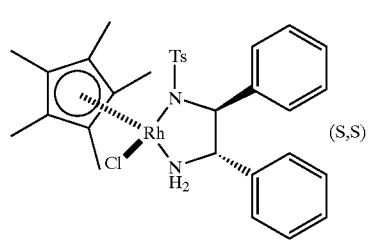

VIIIb (S,S)

in a preselected solvent with an azeotropic mixture of 5:2 formic acid-triethylamine, thereby forming an R enantiomer.

29. The process of claim 28 wherein the molar ratio of substrate/catalyst (S/C) is in the range of over about 100 to 1000 to 1.

30. The process of claim 28 wherein the preselected solvent for the catalyst is a polar solvent.

31. The process of claim 28 wherein the preselected solvent is either acetonitrile or dichloromethane.

32. The process of claim 28 wherein the preselected solvent is supercritical carbon dioxide.

33. The process of claim 28 wherein the target enantiomer of predetermined chirality is obtained in an enantiomeric excess of over 50%.

34. A process of preparing a sultam of predetermined chirality S by asymmetric hydrogenation with a preselected catalyst generated in situ comprising:
(a) reacting a mixture of rhodium dimer of the formula [RhClCp*]$_2$ having the structure (VI)

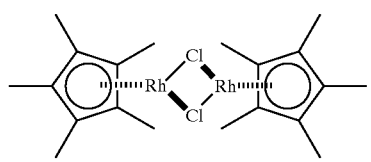

VI and chiral ligand of formula (1R,2R)-N-p-toluenesulfonyl-1,2-diphenylethylenediamine having structure (VIIa) with a lower trialkyl amine;

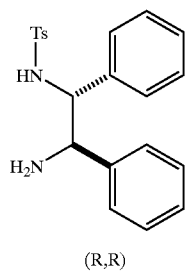

VIIa (R,R)

(b) adding sulfonylimine of structure (III), wherein $R^A$ is selected from the group consisting of hydrogen and a methyl group, and $R^C$ is selected from the group consisting of: a hydrogen, 1–5 halogens, a linear or branched hydrocarbon, hydroxyl, alkoxy, $CF_3$, 1–2 alkyl groups, phenyl, and amide

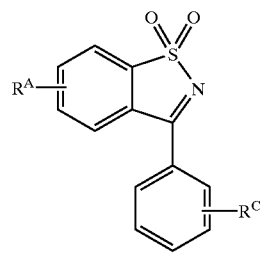

III and an azeotropic mixture of 5:2 formic acid-triethylamine,

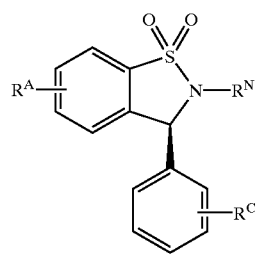

V thereby forming a sultam of formula V having S chirality.

35. The process of claim 34 wherein $R^c$ is hydrogen and the solvent is dichloromethane.

36. The process of claim 34 wherein the solvent is supercritical carbon dioxide.

37. A process of preparing a sultam of predetermined chirality R by asymmetric hydrogenation with a preselected catalyst generated in situ comprising:

(a) reacting a mixture of rhodium dimer of the formula (VI)

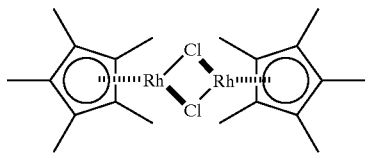

VI and chiral ligand of the formula (1S,2S)-N-p-toluenesulfonyl-1,2-diphenylethylenediamine having structure (VIIb)

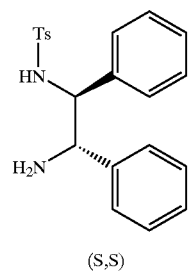

VIIb (S,S)

with a lower trialkyl amine under reactive conditions;

(b) adding a sulfonylimine of structure (III), wherein $R^A$ is selected from the group consisting of hydrogen and a methyl group, and $R^C$ is selected from the group consisting of: a hydrogen, 1–5 halogens, a linear or branched hydrocarbon, hydroxyl, alkoxy, $CF_3$, 1–2 alkyl groups, phenyl, and amide,

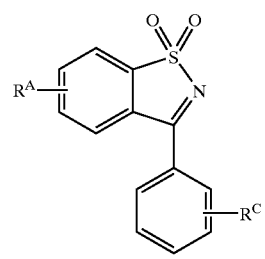

III and an azeotropic mixture of 5:2 formic acid-triethylamine,

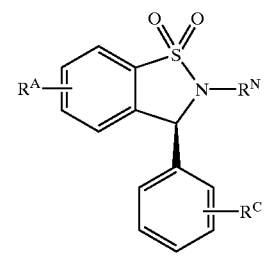

V

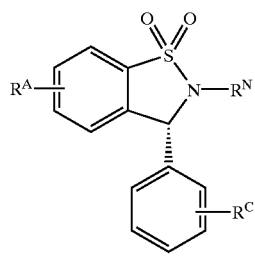

thereby forming said target sultam of formula $V_R$ having R chirality.

38. A method of preparing a sultam of predetermined chirality and having an alkyl substitution of the nitrogen atom of said sultam, from a corresponding sultam lacking a substitution of the nitrogen atom of said corresponding sultam, said target sultam having the formula (V)

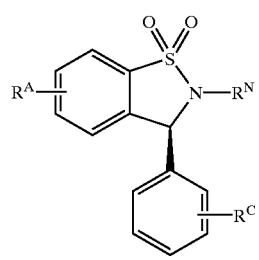

wherein $R^A$ is selected from the group consisting of hydrogen and methyl, where $R^C$ is selected from the group consisting of a hydrogen, 1–5 halogens, a linear or branched hydrocarbon, hydroxyl, alkoxy, $CF_3$, 1–2 alkyl groups, phenyl, and amide and $R^N$ is a methyl group, comprising:

adding to secondary amine of structure (IV)

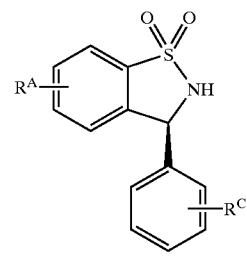

diethyl azodicarboxylate, triphenylphosphine, and an alcohol under an inert atmosphere in a preselected organic solvent, and isolating said target sultam.

39. A process of claim 38 for the preparation of a target sultam wherein $R^c$ is hydrogen, wherein said alcohol is methanol and said solvent is tetrahydrofuran.

40. A process of claim 38 for the preparation of a target sultam wherein $R^c$ is a 3-chloro group, wherein said alcohol is methanol and said solvent is tetrahydrofuran.

41. A method for the preparation of a predetermined target sultam enantiomer of the formula (V),

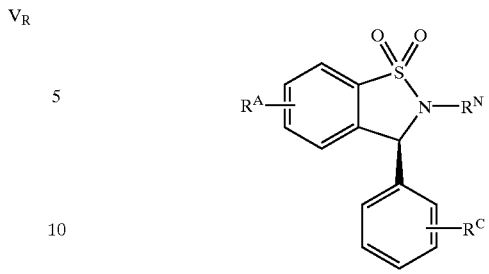

wherein $R^A$ is selected from the group consisting of hydrogen and methyl, where $R^C$ is selected from the group consisting of a hydrogen, 1–5 halogens, a linear or branched hydrocarbon, hydroxyl, alkoxy, $CF_3$, 1–2 alkyl groups, phenyl, and amide and $R^N$ is a methyl group, from a corresponding sultam lacking a methyl substitution of the nitrogen atom comprising:

(a) reacting a secondary amine of structure (IV)

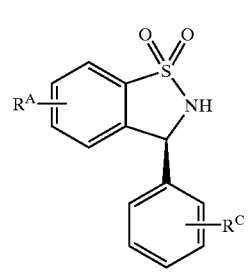

with a weak base in an organic solvent;
adding an alkyl iodide, and isolating said target sultam (V).

42. The process of claim 41 wherein the weak base is cesium carbonate.

43. The process of claim 41 wherein $R^c$ is a 3-bromo group, said alkyl iodide is methyl iodide and said solvent is N,N-dimethylformamide.

44. A process of claim 41 wherein $R^c$ is a 3-fluoro group, said alkyl iodide is methyl iodide, and said solvent is N,N-dimethylformamide.

45. A process of claim 41 wherein $R^c$ is a 3-methyl group, said alkyl iodide is methyl iodide, and said solvent is N,N-dimethylformamide.

46. A process of claim 41 wherein $R^c$ is a 2-methyl group, said alkyl iodide is methyl iodide, and said solvent is N,N-dimethylformamide.

47. A method for preparing a 3-(3-iodophenyl)sultam of formula (X)

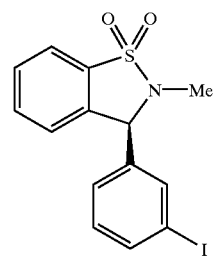

by conversion of a 3-(3-bromophenyl)sultam of formula (Vc) comprising:

(a) dissolving said 3-(3-bromophenyl)sultam of structure (Vc) in degassed toluene, thereby forming a reaction solution;

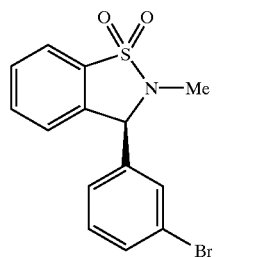

Vc (b) reacting tributylstannane with said reaction solution, thereby obtaining a stannane of structure (IX),
(c) performing an iodination of said stannane of structure (IX) by reacting said stannane with iodine in a solvent in an inert atmosphere;

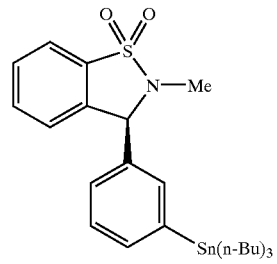

IX (d) and purifying and substantially separating said 3-(3-iodophenyl)sultam (X).

* * * * *